United States Patent
Fischer et al.

(10) Patent No.: US 12,409,214 B2
(45) Date of Patent: *Sep. 9, 2025

(54) IMMUNOGENIC ANTIGENS

(71) Applicant: Longhorn Vaccines and Diagnostics, LLC, Bethesda, MD (US)

(72) Inventors: Jeffrey D. Fischer, Washington, DC (US); Clara J. Sei, Germantown, MD (US); Luke T. Daum, San Antonio, TX (US); Gerald W. Fischer, Bethesda, MD (US)

(73) Assignee: Longhorn Vaccines and Diagnostics, LLC, Bethesda, MD (US)

( * ) Notice: Subject to any disclaimer, the term of this patent is extended or adjusted under 35 U.S.C. 154(b) by 126 days.

This patent is subject to a terminal disclaimer.

(21) Appl. No.: 17/506,254

(22) Filed: Oct. 20, 2021

(65) Prior Publication Data

US 2022/0296696 A1    Sep. 22, 2022

Related U.S. Application Data

(60) Provisional application No. 63/246,360, filed on Sep. 21, 2021, provisional application No. 63/094,472, filed on Oct. 21, 2020, provisional application No. 63/094,116, filed on Oct. 20, 2020.

(51) Int. Cl.
| | |
|---|---|
| *A61K 39/02* | (2006.01) |
| *A61K 39/04* | (2006.01) |
| *A61K 39/09* | (2006.01) |
| *A61K 39/095* | (2006.01) |
| *A61K 39/102* | (2006.01) |
| *A61K 39/116* | (2006.01) |
| *A61K 39/385* | (2006.01) |
| *A61K 47/64* | (2017.01) |
| *A61P 31/16* | (2006.01) |
| *A61P 37/04* | (2006.01) |
| *A61K 39/00* | (2006.01) |
| *A61K 39/145* | (2006.01) |

(52) U.S. Cl.
CPC ............ *A61K 39/116* (2013.01); *A61K 39/04* (2013.01); *A61K 39/092* (2013.01); *A61K 39/095* (2013.01); *A61K 39/102* (2013.01); *A61K 39/385* (2013.01); *A61K 47/6415* (2017.08); *A61K 47/646* (2017.08); *A61P 31/16* (2018.01); *A61P 37/04* (2018.01); *A61K 39/145* (2013.01); *A61K 2039/5252* (2013.01); *A61K 2039/5254* (2013.01); *A61K 2039/53* (2013.01); *A61K 2039/543* (2013.01); *A61K 2039/545* (2013.01); *A61K 2039/55555* (2013.01); *A61K 2039/55566* (2013.01); *A61K 2039/55572* (2013.01); *A61K 2039/575* (2013.01); *A61K 2039/6037* (2013.01); *A61K 2039/6043* (2013.01); *A61K 2039/6068* (2013.01); *A61K 2039/70* (2013.01)

(58) Field of Classification Search
None
See application file for complete search history.

(56) References Cited

U.S. PATENT DOCUMENTS

| | | |
|---|---|---|
| 4,196,265 A | 4/1980 | Koprowski |
| 4,235,244 A | 11/1980 | Abele |
| 4,529,702 A | 7/1985 | Bryan |
| 4,554,101 A | 11/1985 | Hopp |
| 4,634,664 A | 1/1987 | Oestberg |
| 4,634,666 A | 1/1987 | Engleman |
| 4,668,476 A | 5/1987 | Bridgham |
| 4,683,195 A | 7/1987 | Mullis |
| 4,683,202 A | 7/1987 | Mullis |
| 4,707,450 A | 11/1987 | Nason |
| 4,744,982 A | 5/1988 | Hunter |
| 4,746,490 A | 5/1988 | Saneii |
| 4,749,490 A | 6/1988 | Smyth |
| 4,800,159 A | 1/1989 | Mullis |
| 4,803,998 A | 2/1989 | Kezes |
| 4,816,513 A | 3/1989 | Bridgham |
| 4,883,750 A | 11/1989 | Whiteley |
| 4,954,449 A | 9/1990 | Hunter |

(Continued)

FOREIGN PATENT DOCUMENTS

| | | |
|---|---|---|
| CN | 101785857 | 3/2010 |
| CN | 106039301 | 6/2016 |

(Continued)

OTHER PUBLICATIONS

Schaap-Johansen et al (Front. Immunol. vol. 12, Sep. 2021. pp. 1-11).*
Devos et al., (Proteins: Structure, Function and Genetics, 2000, vol. 41: 98-107).*
Whisstock et al., (Quarterly Reviews of Biophysics 2003, vol. 36 (3): 307-340,).*

(Continued)

*Primary Examiner* — Jennifer E Graser
(74) *Attorney, Agent, or Firm* — Remenick PLLC

(57) ABSTRACT

The invention relates to composite antigens comprising an antigen obtained or derived from an antigenic epitope of one or more pathogens that induces an immune response in a mammal, an antigen obtained or derived from bacterial cell wall material that induces an immune response in a mammal such as LTA, PNG or LPS, and a T cell stimulating antigen such as CRM. Preferably the composite antigen comprises an immunogenic composition or a vaccine that is effective against the pathogen or can generate antibodies that can be collected that are protective against infection by the pathogen. In addition, the invention relates to vaccines comprising composite antigens and to method for treating and preventing an infection.

28 Claims, 14 Drawing Sheets

Specification includes a Sequence Listing.

(56) References Cited

U.S. PATENT DOCUMENTS

| | | |
|---|---|---|
| 4,996,143 A | 2/1991 | Heller |
| 5,091,316 A | 2/1992 | Monthony |
| 5,108,927 A | 4/1992 | Dorn |
| 5,145,684 A | 9/1992 | Liversidge |
| 5,149,653 A | 9/1992 | Roser |
| 5,163,441 A | 11/1992 | Monthony |
| 5,168,039 A | 12/1992 | Crawford |
| 5,182,109 A | 1/1993 | Tamura |
| 5,186,898 A | 2/1993 | Bridgham |
| 5,234,809 A | 8/1993 | Boom |
| 5,399,363 A | 3/1995 | Liversidge |
| 5,422,241 A | 6/1995 | Goldrick |
| 5,482,856 A | 1/1996 | Fell, Jr. |
| 5,503,841 A | 4/1996 | Doyle |
| 5,543,158 A | 8/1996 | Gref |
| 5,545,555 A | 8/1996 | Racioppi |
| 5,552,157 A | 9/1996 | Yagi |
| 5,565,213 A | 10/1996 | Nakamori |
| 5,565,322 A | 10/1996 | Heller |
| 5,567,434 A | 10/1996 | Szoka, Jr. |
| 5,571,511 A | 11/1996 | Fischer |
| 5,627,071 A | 5/1997 | Triva |
| 5,641,515 A | 6/1997 | Ramtoola |
| 5,656,016 A | 8/1997 | Ogden |
| 5,679,356 A | 10/1997 | Bonnem |
| 5,691,299 A | 11/1997 | Fabry |
| 5,697,899 A | 12/1997 | Hillman |
| 5,702,944 A | 12/1997 | Racioppi |
| 5,736,333 A | 4/1998 | Livak |
| 5,738,868 A | 4/1998 | Shinkarenko |
| 5,741,516 A | 4/1998 | Webb |
| 5,770,219 A | 6/1998 | Chiang |
| 5,779,708 A | 7/1998 | Wu |
| 5,783,208 A | 7/1998 | Venkateshwaran |
| 5,785,973 A | 7/1998 | Bixler |
| 5,785,975 A | 7/1998 | Parikh |
| 5,795,582 A | 8/1998 | Wright |
| 5,795,587 A | 8/1998 | Gao |
| 5,797,898 A | 8/1998 | Santini, Jr. |
| 5,800,810 A | 9/1998 | Doyle |
| 5,849,489 A | 12/1998 | Heller |
| 5,891,624 A | 4/1999 | Huang |
| 5,945,515 A | 8/1999 | Chomczynski |
| 5,955,074 A | 9/1999 | Fischer |
| 6,033,673 A | 3/2000 | Clements |
| 6,060,068 A | 5/2000 | Doyle |
| 6,136,585 A | 10/2000 | Ball |
| 6,162,603 A | 12/2000 | Heller |
| 6,204,375 B1 | 3/2001 | Lader |
| 6,306,404 B1 | 10/2001 | LaPosta |
| 6,312,395 B1 | 11/2001 | Tripp |
| 6,440,423 B1 | 8/2002 | Clements |
| 6,451,325 B1 | 9/2002 | Van Nest |
| 6,500,432 B1 | 12/2002 | Dalemans |
| 6,534,065 B1 | 3/2003 | Makin |
| 6,572,866 B1 | 6/2003 | Torcia |
| 6,602,510 B1 | 8/2003 | Fikes |
| 6,603,908 B2 | 8/2003 | Dallas |
| 6,603,998 B1 | 8/2003 | King |
| 6,610,293 B1 | 8/2003 | Fischer |
| 6,617,170 B2 | 9/2003 | Augello |
| 6,632,432 B1 | 10/2003 | Fischer |
| 6,689,363 B1 | 2/2004 | Sette |
| 6,713,068 B1 | 3/2004 | Audonnet |
| 6,759,241 B1 | 7/2004 | Hone |
| 6,776,959 B1 | 8/2004 | Helftenbein |
| 6,780,421 B1 | 8/2004 | Haensler |
| 6,793,928 B1 | 9/2004 | van Scharrenburg |
| 6,855,321 B1 | 2/2005 | Rappuoli |
| 6,939,543 B2 | 9/2005 | Fischer |
| 7,090,853 B2 | 8/2006 | Kapp |
| 7,122,640 B2 | 10/2006 | Gjerde |
| 7,223,409 B2 | 5/2007 | Nagata |
| 7,279,162 B1 | 10/2007 | Fischer |
| 7,311,671 B2 | 12/2007 | Jung |
| 7,351,413 B2 | 4/2008 | Page |
| 7,357,936 B1 | 4/2008 | Garcon |
| 7,361,352 B2 | 4/2008 | Birkett |
| 7,438,919 B2 | 10/2008 | Dowling |
| 7,541,194 B2 | 6/2009 | Mink |
| 7,547,512 B2 | 6/2009 | Peiris |
| 7,648,681 B2 | 1/2010 | Meyer |
| 7,767,804 B2 | 8/2010 | Bair, Jr. |
| 7,794,001 B2 | 9/2010 | Blackwell |
| 8,080,645 B2 | 12/2011 | Fischer |
| 8,084,443 B2 | 12/2011 | Fischer |
| 8,097,419 B2 | 1/2012 | Fischer |
| 8,293,467 B2 | 10/2012 | Fischer |
| 8,415,330 B2 | 4/2013 | Fischer |
| 8,652,782 B2 | 2/2014 | Fischer |
| 8,669,240 B2 | 3/2014 | Fischer |
| 8,821,885 B2 | 9/2014 | Fischer |
| 8,883,165 B2 | 11/2014 | Kaminaka |
| 9,080,204 B2 | 7/2015 | Fischer |
| 9,212,399 B2 | 12/2015 | Fischer |
| 9,365,904 B2 | 6/2016 | Fischer |
| 9,370,775 B2 | 6/2016 | Harvey |
| 9,416,416 B2 | 8/2016 | Fischer |
| 9,481,912 B2 | 11/2016 | Fischer |
| 9,522,962 B2 | 12/2016 | Ossendorp |
| 9,598,462 B2 | 3/2017 | Fischer |
| 9,683,256 B2 | 6/2017 | Fischer |
| 9,814,766 B2 | 11/2017 | Fischer |
| 9,821,047 B2 | 11/2017 | Fischer |
| 9,976,136 B2 | 5/2018 | Fischer |
| 10,004,799 B2 | 6/2018 | Fischer |
| 10,370,437 B2 | 8/2019 | Fischer |
| 10,414,819 B2 | 9/2019 | Fischer |
| 10,596,250 B2 | 3/2020 | Fischer |
| 10,787,504 B2 | 9/2020 | Fischer |
| 10,870,878 B2 | 12/2020 | Fischer |
| 2002/0082395 A1 | 6/2002 | Fischer |
| 2004/0013673 A1 | 1/2004 | Fischer |
| 2004/0038269 A1 | 2/2004 | Birnboim |
| 2004/0101859 A1 | 5/2004 | Moon |
| 2004/0101869 A1 | 5/2004 | Berg et al. |
| 2004/0126789 A1 | 7/2004 | Park |
| 2004/0214272 A1 | 10/2004 | La Rosa |
| 2004/0223976 A1 | 11/2004 | Bianchi |
| 2005/0007948 A1 | 1/2005 | Heineman |
| 2005/0090009 A1 | 4/2005 | Cormier |
| 2005/0112656 A1 | 5/2005 | Iwaki |
| 2005/0123928 A1 | 6/2005 | Das |
| 2005/0169941 A1 | 8/2005 | Lees |
| 2005/0227269 A1 | 10/2005 | Lloyd, Jr. |
| 2006/0002939 A1 | 1/2006 | Fischer |
| 2006/0014185 A1 | 1/2006 | Ollikka |
| 2006/0105468 A1 | 5/2006 | Winkler |
| 2006/0121468 A1 | 6/2006 | Allnutt |
| 2006/0134648 A1 | 6/2006 | Chou et al. |
| 2006/0286557 A1 | 12/2006 | Basehore |
| 2007/0072229 A1 | 3/2007 | Bialozynski |
| 2007/0102946 A1 | 5/2007 | Blackwell |
| 2007/0172835 A1 | 7/2007 | McBride |
| 2007/0202497 A1 | 8/2007 | Renuart |
| 2007/0202511 A1 | 8/2007 | Chen |
| 2007/0286871 A1 | 12/2007 | Hickle |
| 2007/0292447 A1 | 12/2007 | Bercovier |
| 2008/0032921 A1 | 2/2008 | Alexander |
| 2008/0050737 A1 | 2/2008 | Arieli |
| 2008/0069821 A1 | 3/2008 | Yang |
| 2008/0075708 A1 | 3/2008 | Yu |
| 2008/0107665 A1 | 5/2008 | Suckow |
| 2008/0107687 A1 | 5/2008 | Poulet |
| 2008/0118531 A1 | 5/2008 | Hoffmann |
| 2008/0139789 A1 | 6/2008 | Fischer |
| 2008/0145373 A1 | 6/2008 | Arumugham |
| 2008/0181914 A1 | 7/2008 | Eichhorn |
| 2008/0260763 A1 | 10/2008 | Felgner |
| 2009/0081202 A1 | 3/2009 | Fischer |
| 2009/0098527 A1 | 4/2009 | Fischer |
| 2009/0202553 A1 | 8/2009 | Morrow |
| 2009/0233309 A1 | 9/2009 | Fischer et al. |
| 2010/0151477 A1 | 6/2010 | Cawthon |

(56) References Cited

U.S. PATENT DOCUMENTS

| | | |
|---|---|---|
| 2010/0221822 A1 | 9/2010 | Fischer |
| 2010/0247546 A1 | 9/2010 | Fischer |
| 2010/0311739 A1 | 12/2010 | Gunaratnan |
| 2011/0281754 A1 | 11/2011 | Fischer |
| 2012/0088231 A1 | 4/2012 | Fischer |
| 2012/0100529 A1 | 4/2012 | Fischer |
| 2012/0107799 A1 | 5/2012 | Daum |
| 2012/0115126 A1 | 5/2012 | Fischer |
| 2013/0195909 A1 | 8/2013 | Longhorn |
| 2017/0073738 A1 | 3/2017 | Fischer |
| 2017/0232091 A1 | 8/2017 | Aguiar |
| 2020/0239931 A1 | 7/2020 | Birnboim |
| 2021/0079450 A1 | 3/2021 | Daum |
| 2021/0246174 A1 | 8/2021 | Longhorn |

FOREIGN PATENT DOCUMENTS

| | | |
|---|---|---|
| CN | 106075420 | 6/2016 |
| EP | 0702564 | 3/2000 |
| WO | WO2019/006022 | 1/2019 |

OTHER PUBLICATIONS

Witowski et al., (Biochemistry 38:11643-11650, 1999).*
Kisselev L., (Structure, 2002, vol. 10: 8-9).*
Greenspan et al (Nature Biotechnology 7: 936-937, 1999).*
Chothia et al (The Embo Journal, 1986, 5/4:823-26).*
International Preliminary Search Report Application No. PCT/US2021/55832 dated Mar. 17, 2022.
International Preliminary Opinion for Application No. PCT/US2021/55832 dated Mar. 17, 2022.
Office action of GB Application No. GB 2306776.2 dated Sep. 4, 2024.
D2. Vaccine, vol. 37, No. 31, 2019, Yi et al., "Immunization with a peptide mimicking Lipoteichoic acid protects mice against *Staphylococcus aureus* infection", pp. 4325-4335.
D3. Infection, Genetics and Evolution, vol. 48, 2016, Hajighahramani et al., "Immunoinformatics analysis and in silico designing of a novel multi-epitope peptide vaccine against *Staphylococcus aureus*", pp. 83-94.
Damien Devos et al., Proteins: Structure, Function, and Genetics, 41:98-107 (2000).
Andrzej Witkowski et al., Biochemistry38:11643-11650 (1999).
James C, Whisstock et al., Quarterly Review of Biophysics 36:3 307-340 (2003).
Lev Kisselev, Structure vol. 10, 8-9, Jan. 2002.
U.S. Appl. No. 17/506,237 Office action dated Jan. 12, 2024.
U.S. Appl. No. 17/506,237 Office action dated Jul. 1, 2024.
U.S. Appl. No. 17/506,237 Office action dated Oct. 22, 2024.
Search Report of IE Application No. 2024/0275 dated Oct. 8, 2024.
Written Opinion of IE Application No. 2024/0275 dated Oct. 8, 2024.
Office action of GB Application No. GB 2306776.2 dated Dec. 4, 2024.
Office action of GB Application No. GB2306776.2 dated Mar. 4, 2025.
Office action of GB Application No. GB2306776.2 dated Jun. 2, 2025.
Search Report of IE Application No. 2024/0275 dated Mar. 11, 2025.
Examination Report of IE Application No. 2024/0275 dated Mar. 11, 2025.
Office action of U.S. Appl. No. 17/506,237 dated Mar. 20, 2025.
Office action of GB Application No. GB2508531.7dated Jun. 26, 2025.
Office action of U.S. Appl. No. 17/506,237 dated Jul. 3, 2025.

* cited by examiner

| MOUSE ID | IMMUNOGEN | MABs GENERATED |
|---|---|---|
| M1435 | TB Pep01-CRM, 50μg, SQ | CLONE 1: LD7 I BB2 |
| | | SUBCLONE 1: LD7 I BB2 I B9 |
| | | CLONE 2: CA6 II GA8 |
| | | SUBCLONE 2: CA6 II GA8 I A5 |

*FIG. 8*

| MAB CONC. | % OPSONOPHAGOCYTIC KILLING ACTIVITY BY TWO DIFFERENT ANTI-TB Pep01 MABs | |
|---|---|---|
| µg/mL | MAD LD7 | MAB CA6 |
| 250 | 44 | 27 |
| 200 | 76 | 58 |
| 175 | 62 | 63 |
| 150 | 72 | 10 |
| 100 | 72 | 40 |
| 75 | 76 | 46 |
| 50 | 75 | 22 |
| 25 | 52 | 51 |
| 12.5 | 56 | 43 |
| 10 | 71 | 63 |
| 5 | 74 | 55 |
| 1 | 64 | 49 |
| 0.1 | 73 | 47 |
| 0.05 | 41 | 61 |

*FIG. 14*

SEQUENCE LISTING

```
<160> NUMBER OF SEQ ID NOS: 29

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Glu Phe Ala Tyr Gly Ser Phe Val Arg Thr Val Ser Leu Pro Val
1               5                   10                  15

Gly Ala Asp Glu
            20
```

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Glu Phe Ala Tyr Gly Ser Phe Met Arg Ser Val Thr Leu Pro Pro
1               5                   10                  15

Gly Ala Asp Glu
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Glu Phe Ser Tyr Gly Ser Phe Val Arg Thr Val Ser Leu Pro Gly
1               5                   10                  15

Gly Ala Asp Glu
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Glu Phe Ser Tyr Gly Ser Phe Val Arg Thr Val Ser Leu Pro Ala
1               5                   10                  15

Gly Ala Asp Glu
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Glu Phe Ser Tyr Gly Ser Phe Val Arg Thr Val Thr Leu Pro Thr
1               5                   10                  15

Asp Ala Asp Glu
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Ser Glu Phe Ser Tyr Gly Ser Phe Ala Arg Thr Val Ser Leu Pro Ala
1               5                   10                  15

Gly Ala Asn Glu
            20
```

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Trp Arg Met Tyr Phe Ser His Arg His Ala His Leu Arg Ser Pro
1               5                   10                  15
```

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Trp His Trp Arg His Arg Ile Pro Leu Gln Leu Ala Ala Gly Arg
1               5                   10                  15
```

<210> SEQ ID NO 9
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Trp Arg Met Tyr Phe Ser His Arg His Ala His Leu Arg Ser Pro Gln
1               5                   10                  15

Tyr Ile Lys Ala Asn Ser Lys Phe Ile Gly Ile Thr Glu
            20                  25
```

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Trp His Trp Arg His Arg Ile Pro Leu Gln Leu Ala Ala Gly Arg Gln
1               5                   10                  15

Tyr Ile Lys Ala Asn Ser Lys Phe Ile Gly Ile Thr Glu
            20                  25
```

<210> SEQ ID NO 11
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Gln Tyr Ile Lys Ala Asn Ser Lys Phe Ile Gly Ile Thr Glu Trp Arg
1               5                   10                  15

Met Tyr Phe Ser His Arg His Ala His Leu Arg Ser Pro
            20                  25
```

<210> SEQ ID NO 12
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Gln Tyr Ile Lys Ala Asn Ser Lys Phe Ile Gly Ile Thr Glu Trp His
1               5                   10                  15

Trp Arg His Arg Ile Pro Leu Gln Leu Ala Ala Gly Arg
            20                  25
```

<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Trp Arg Met Tyr Phe Ser His Arg His Ala His Leu Arg Ser Pro Gln
1               5                   10                  15

Tyr Ile Lys Ala Asn Ser Lys Phe Ile Gly Ile Thr Glu Trp His Trp
            20                  25                  30

Arg His Arg Ile Pro Leu Gln Leu Ala Ala Gly Arg
        35                  40
```

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Trp Arg Met Tyr Phe Ser His Arg His Ala His Leu Arg Ser Pro Trp
1               5                   10                  15

His Trp Arg His Arg Ile Pro Leu Gln Leu Ala Ala Gly Arg
            20                  25                  30
```

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Trp His Trp Arg His Arg Ile Pro Leu Gln Leu Ala Ala Gly Arg Trp
1               5                   10                  15

Arg Met Tyr Phe Ser His Arg His Ala His Leu Arg Ser Pro
            20                  25                  30
```

<210> SEQ ID NO 16

```
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Trp Arg Met Tyr Phe Ser His Arg His Ala His Leu Arg Ser Pro Trp
1               5                   10                  15

His Trp Arg His Arg Ile Pro Leu Gln Leu Ala Ala Gly Arg Gln Tyr
            20                  25                  30

Ile Lys Ala Asn Ser Lys Phe Ile Gly Ile Thr Glu
        35                  40

<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Tyr Ile Lys Ala Asn Ser Lys Phe Ile Gly Ile Thr Glu Trp Arg
1               5                   10                  15

Met Tyr Phe Ser His Arg His Ala His Leu Arg Ser Pro Trp His Trp
            20                  25                  30

Arg His Arg Ile Pro Leu Gln Leu Ala Ala Gly Arg
        35                  40

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

His Ser Phe Lys Trp Leu Asp Ser Pro Arg Leu Arg
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Ser Leu Thr Glu Trp Ser Met Trp Tyr Arg His
1               5                   10

<210> SEQ ID NO 20
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ile Ser Leu Thr Glu Trp Ser Met Trp Tyr Arg His Gln Tyr Ile Lys
1               5                   10                  15
```

-continued

Ala Asn Ser Lys Phe Ile Gly Ile Thr Glu His Ser Phe Lys Trp Leu
            20                  25                  30

Asp Ser Pro Arg Leu Arg
        35

<210> SEQ ID NO 21
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Tyr Ile Lys Ala Asn Ser Lys Phe Ile Gly Ile Thr Glu His Tyr
1               5                   10                  15

Glu Glu Cys Ser Cys Tyr His Ser Phe Lys Trp Leu Asp Ser Pro Arg
            20                  25                  30

Leu Arg

<210> SEQ ID NO 22
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser Glu Phe Ala Tyr Gly Ser Phe Val Arg Thr Val Ser Leu Pro Val
1               5                   10                  15

Gly Ala Asp Glu His Ser Phe Lys Trp Leu Asp Ser Pro Arg Leu Arg
            20                  25                  30

<210> SEQ ID NO 23
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser Glu Phe Ala Tyr Gly Ser Phe Val Arg Thr Val Ser Leu Pro Val
1               5                   10                  15

Gly Ala Asp Glu His Ser Phe Lys Trp Leu Asp Ser Pro Arg Leu Arg
            20                  25                  30

Gln Tyr Ile Lys Ala Asn Ser Lys Phe Ile Gly Ile Thr Glu
        35                  40                  45

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Glu Phe Ala Tyr Gly Ser Phe Val Arg Thr Val Ser Leu Pro Val
1               5                   10                  15

Gly Ala Asp Glu
            20

<210> SEQ ID NO 25
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Asn Leu Phe Ile Ala Pro Trp Gly Val Ile His His Pro His Tyr
1               5                   10                  15

Glu Glu Cys Ser Cys Tyr
            20

<210> SEQ ID NO 26
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser Glu Phe Ala Tyr Gly Ser Phe Val Arg Thr Val Ser Leu Pro Val
1               5                   10                  15

Gly Ala Asp Glu Gly Asn Leu Phe Ile Ala Pro Trp Gly Val Ile His
            20                  25                  30

His Pro His Tyr Glu Glu Cys Ser Cys Tyr
        35                  40

<210> SEQ ID NO 27
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser Leu Leu Thr Glu Val Glu Thr Pro Ile Arg Asn Glu Trp Gly Leu
1               5                   10                  15

Leu Thr Glu Val Glu Thr Pro Ile Arg Gln Tyr Ile Lys Ala Asn Ser
            20                  25                  30

Lys Phe Ile Gly Ile Thr Glu
        35

<210> SEQ ID NO 28
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Asn Leu Phe Ile Ala Pro Trp Gly Val Ile His His Pro His Tyr
1               5                   10                  15

Glu Glu Cys Ser Cys Tyr Gln Tyr Ile Lys Ala Asn Ser Lys Phe Ile
            20                  25                  30

Gly Ile Thr Glu
        35

```
<210> SEQ ID NO 29
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Tyr Ile Lys Ala Asn Ser Lys Phe Ile Gly Ile Thr Glu Gly Asn
1               5                   10                  15

Leu Phe Ile Ala Pro Trp Gly Val Ile His His Pro His Tyr Glu Glu
            20                  25                  30

Cys Ser Cys Tyr
            35
```

IMMUNOGENIC ANTIGENS

REFERENCE TO RELATED APPLICATIONS

This application claims priority to U.S. Provisional Application No. 63/094,116 filed Oct. 20, 2020, U.S. Provisional Application No. 63/094,472 filed Oct. 21, 2020, and U.S. Provisional Application No. 63/246,360 filed Sep. 21, 2021, the entirety of each of which is specifically incorporated by reference.

SEQUENCE LISTING

The instant application contains a Sequence Listing which has been submitted electronically in ASCII format and is hereby incorporated by reference in its entirety. Said ASCII copy, created on Oct. 15, 2021, is named 3022-051_US-_SL.txt and is 11,762 bytes in size.

BACKGROUND

Field of the Invention

The present invention is directed to composite antigens composed of a plurality of epitopes, and to tools and methods for generating an immune response with the composite antigens. The invention is also directed to compositions comprising composite antigens containing epitopes, composite epitopes, and mimotopes specific to one or more pathogens including epitopes, composite epitopes, and mimotopes specific to bacterial cell wall material, which may include T cell stimulating epitopes and/or adjuvants. In particular, the invention is directed to immunogenic compositions comprising composite antigens, vaccines comprising composite antigens, antibodies to composite antigens, and methods of generating an immune response with composite antigens.

Description of the Background

Microbial pathogens are a primary source of infectious disease in animals. Pathogens and their hosts constantly adapt to one another in an endless competition for survival and propagation. Certain pathogens have become enormously successful at infecting mammalian hosts and surviving exposure to the host immune response, even over periods of years or decades. These extremely successful mammalian pathogens include but are not limited to bacteria, viruses, and unicellular and multicellular eukaryotes such as fungi and parasitic organisms.

Currently, the spread of pathogenic organisms is controlled in animal populations by vaccination and/or treatment with one or more immunogenic compositions such as vaccines. Vaccines containing inactivated or killed organisms simply antigen are currently in use worldwide and especially promoted for use by high-risk groups such as infants, the elderly, those without adequate health care and immunocompromised individuals. Many vaccines contain microorganisms inactivated by chemical means and the antigens purified. The World Health Organization (WHO) provides regular reports of the specific serotypes targeted for vaccine development to those believed to be most prevalent in a particular region and thereby maximize overall world efficacy. Historically, pandemics are spread to different continents within months, and future pandemics are likely to spread even faster due to increased international travel. It is likely inevitable that an effective vaccine made by conventional means will be unavailable or in very short supply during the first wave of any future widespread outbreak or pandemic.

Gram-positive bacteria are a major cause of nosocomial infection. The most common pathogenic isolates in hospitals include *Enterococcus* spp., *Staphylococcus aureus*, coagulase-negative *Staphylococci*, and *Streptococcus pneumoniae* (e.g., Principles and Practice of Infectious Diseases, 4th ed. Mandell G L, Bennett J E, Dolin R, ed. Churchill Livingstone, New York 1995), many strains of which are resistant to one or more antibiotics. *Enterococcus* spp. are part of the normal gut flora in humans. Of the more than seventeen *Enterococcal* species, only *E. faecalis* and *E. faecium* commonly colonize and infect humans in detectable numbers (*E. faecalis* is isolated from approximately 80% of human infections, and *E. faecium* from most of the rest).

*Staphylococci* cause a wide variety of diseases ranging from superficial abscesses (e.g., boils, styes, furuncles and other localized abscesses) to deeper infections (e.g., osteomyelitis, pneumonia, endocarditis, urinary tract infections, septic arthritis, meningitis, post-operative wound infections, septicemia and food poisoning). *S. aureus* is a major cause of hospital acquired (nosocomial) infection of surgical wounds and *S. epidermidis* causes infections associated with indwelling medical devices. (See, e.g., Silverstein et al., 1990; Patti et al., 1994; Dann et al., 1994.).

Multiple antibiotic resistance is increasingly common in *S. aureus* and *S. epidermidis*. Hospital strains of *Staphylococcus* are often resistant to many different antibiotics. *S. epidermidis* nosocomial isolates are also often resistant to several antibiotics including methicillin. In addition, *S. aureus* expresses resistance to antiseptics and disinfectants, such as quaternary ammonium compounds, that may aid its survival in the hospital environment.

*Mycobacterium tuberculosis* (MTB) also stain weakly gram-positive and are a pathogenic bacterial species in the family Mycobacteriaceae and the causative agent of most cases of tuberculosis (TB). Other species of this genus include *M. smegmatis*, a non-pathogenic species utilized in research labs, and *M. leprae*, the causative agent of leprosy. MTB was first discovered in 1882 by Robert Koch, *M. tuberculosis* has an unusual, complex, lipid rich, capsule which makes the cells mostly impervious to Gram staining. Acid-fast detection techniques are used to make the diagnosis instead. The physiology of *M. tuberculosis* is highly aerobic and requires significant levels of oxygen to remain viable. Primarily a pathogen of the mammalian respiratory system, MTB is generally inhaled and, in five to ten percent of individuals, will progress to an acute pulmonary infection. The remaining individuals will either clear the infection completely or the infection may become latent. It is not clear how the immune system controls MTB, but cell mediated immunity is believed to play a critical role (Svenson et al., Human Vaccines, 6-4:309-17, 2010). Common diagnostic methods for TB are the tuberculin skin test, acid-fast stain and chest radiographs.

*M. tuberculosis* requires oxygen to proliferate and does not retain typical bacteriological stains due to high lipid content of its cell wall. While *Mycobacteria* do not fit the Gram-positive category from an empirical standpoint (i.e., they do not retain the crystal violet stain), they are classified as acid-fast Gram-positive bacteria due to their lack of an outer cell membrane.

Gram-negative bacteria are bacteria that do not retain the crystal violet stain used in the Gram staining method of bacterial differentiation. They are characterized by their cell envelopes, which are composed of a thin peptidoglycan cell wall sandwiched between an inner cytoplasmic cell membrane and a bacterial outer membrane. Gram-negative bacteria are found everywhere, in virtually all environments on Earth that support life. The gram-negative bacteria include the model organism *Escherichia coli*, as well as many pathogenic bacteria, such as *Pseudomonas aeruginosa*, *Chlamydia trachomatis*, and *Yersinia pestis*. They are an important medical challenge, as their outer membrane protects them from many antibiotics (including penicillin); detergents that would normally damage the peptidoglycans of the (inner) cell membrane; and lysozyme, an antimicrobial enzyme produced by animals that forms part of the innate immune system. Additionally, the outer leaflet of this membrane comprises a complex lipopolysaccharide (LPS) whose lipid A component can cause a toxic reaction when these bacteria are lysed by immune cells. This toxic reaction can include fever, an increased respiratory rate, and low blood pressure, which can be a life-threatening condition known as septic shock.

Due in large part to the advent of high-speed sequencing techniques, polynucleotide and polypeptide sequences from all of these pathogens including various strains are found within publicly-available databases such as the National Center for Biotechnology Information (National Library of Medicine, National Institutes of Health, Bethesda, MD, USA). Stocks of bacteria and other organisms may be obtained from the American Type Culture Collection (Manassas, VA, USA), and other publicly available sources.

Septic shock is a common cause of death in patients in intensive care units and is caused by bacterial cell wall components to include peptidoglycan (PGN) and lipoteichoic acid (LTA) of gram-positive bacteria and LPS of gram-negative bacteria. These bacteria alone or in combination can invade the bloodstream or release cell wall components into the bloodstream and tissues causing shock and multi organ failure. Using ultra-purified PGN and non-purified PGN that contains LTA, specific antibodies specific for PGN and LTA have been developed that bind each of these cell wall components. In addition, antibodies to cell wall components can promote opsonophagocytic killing activity (OPKA) of bacteria and promote clearance from the blood. Antibodies to LTA or PGN can enhance immunity to gram-positive bacteria that promotes OPKA, while also binding cell wall fragments from dead and damaged bacteria. When such antibodies are unavailable or administered too late, cell wall components act to induce cytokines and chemokines that cause over production of the inflammatory response and promote tissue damage and shock. This overstimulation of the immune response is often referred to as a cytokine storm and extremely harmful to the host, often with deadly consequences.

Vaccines capable of producing a protective immune response to a microorganism have been produced in the last half century. Vaccines have been very effective in protecting people from a wide variety of diseases, whether caused by virus, bacteria, or fungus. The ability of vaccines to induce specific protection against such a wide range of pathogenic organisms results from their ability to stimulate specific humoral antibody responses, as well as cell-mediated responses. Certain agents can stimulate an immune response with minimal chemical modifications, for example, tetanus toxoid, which is immunogenic even in the absence of an adjuvant. Other important agents are either non-immunogenic or poorly immunogenic, but they can be converted into immunogenic molecules or constructs, in which form they can induce vigorous immune responses. For example, most polysaccharides are poorly immunogenic. After they are coupled to proteins, however, the resulting construct becomes immunogenic. The conjugation of proteins to polysaccharides converts the polysaccharide from a weakly immunogenic T-cell independent antigen to a T-cell dependent antigen that recruits T-cell help, and thus stimulates heightened immune responses (e.g., see J. M. Cruse, et al. (Editors), Conjugate Vaccines, Karger, Basel, (1989); R. W. Ellis, et al. (Editors), Development and Clinical Uses of Haemophilus B Conjugate Vaccines, Marcel Dekker, N.Y. (1994)). Well-known T cell stimulating agents include but are not limited to tetanus toxin, tetanus toxin heavy chain proteins, diphtheria toxoid (e.g., natural and recombinant forms of CRM), tetanus toxoid, *Pseudomonas* exoprotein A, *Pseudomonas aeruginosa* toxoid, *Bordetella pertussis* toxoid, *Clostridium perfringens* toxoid, *Escherichia coli* heat-labile toxin B subunit, *Neisseria meningitidis* outer membrane complex, Hemophilus influenzae protein D, Flagellin Fli C, Horseshoe crab Haemocyanin, and fragments, derivatives, and modifications thereof including both natural and recombinant forms.

Conjugation of a T cell stimulating protein and a polysaccharide can provide advantageous results. For example, protein-polysaccharide conjugates enhance the antibody response not only to the polysaccharide component, but also to the protein component (e.g., U.S. Pat. No. 5,585,100). This effect also is described in A. Lees, et al., "Enhanced Immunogenicity of Protein-Dextran Conjugates: I. Rapid Stimulation of Enhanced Antibody Responses to Poorly Immunogenic Molecules," Vaccine, Vol. 12, No. 13, (1994), pp. 1160 1166.

With the continual emergence (or re-emergence) of different bacterial pathogens, new conjugate vaccines are continually in demand. Because of rapid mutation and variability of bacterial strains (including serotypes, sub-strains, etc.), it has been extremely difficult and at times not possible to identify the antigenic moieties of emergent organisms in sufficient time to develop a suitable vaccine. Polypeptides and polynucleotides of newly emergent or re-emergent bacterial strains (especially sequences of antigenic genes) are highly desirable. Certain antigens tend to interact most strongly with the host's internal environment and dominate the host immune response and are often those that protect the microbe from the host immune system. These immune-dominant antigens are generally most desirable for a vaccine. Conversely, non-immunodominant antigens are those that are capable of raising a host immune response, but account for only a small amount of the total immune response. This is thought to happen because the non-immunodominant antigens are at least partially shielded from the host immune system, as in the case of an antigen that is located in a cleft or fold of the microbial surface or is surrounded by protruding elements of the microbe. Non-immunodominant antigens tend to show less mutation in response to host immune pressure than do immunodominant antigens.

The CDC and the leading authorities on disease prevention in the world recommend the single best way of preventing an infection is through regular vaccinations. Conventional vaccines, however, typically target single antigens. The ineffectiveness of conventional vaccines may also be due, in part, to antigenic drift of the microorganism. As a result, many humans may find themselves susceptible to the microbial infections and cytokine storms without an effective method of treatment. This scenario is particularly concerning with respect to highly pathogenic microorganisms.

It would be advantageous to administer a vaccine that provides protection against one or more microorganisms while at the same time reducing the inflammatory response caused by the presence of cells surface material. It would also be advantageous to administer a single or limited number of vaccinations that would provide effective protection across a selection of different pathogens and a vaccine that could be effective in those individuals with limited immune system function. Such vaccines would be useful to treat many individuals and populations and may be useful to compliment conventional vaccines, all to provide comprehensive protection to as many individuals as possible against existing as well as new and emerging pathogens across a population.

SUMMARY OF THE INVENTION

The present invention provides new and useful compositions, as well as tools and methods for generating an immune response. In particular, the invention provides immunogenic compositions, peptides, vaccines, and methods containing and developed from antigenic regions of one or more pathogens.

One embodiment of the invention is directed to an antigen comprising a peptide. The peptide contains two or more antigenic epitopes or one or more epitopes coupled to one or more mimotopes, which preferable may be along a contiguous sequence. Antigenic peptides/compositions as described herein further comprises a T cell stimulating epitope and/or an adjuvant. Any of these epitopes may be or include a composite epitope. Immunogenic antigens of the disclosure induce an immune response in a mammal that generates or enhances immunity to infection attributable to the pathogen that contains the epitope and/or the pathogen which contains an epitope from which the mimotope is derived, which may be the same or a different pathogen.

Preferably immunogenic peptides/compositions contain one or more antigenic epitopes specific for one or more cell wall antigens (CWA) and an adjuvant and/or a T cell stimulating antigen/epitope (TCSA) in any combination. For example: CWA plus adjuvant; CWA-TCSA; TCSA-CWA-TCSA; CWA-TCSA-CWA and other combinations and multiples thereof. Peptides and composites can include one or more epitopes of a pathogen specific antigen (PSA), again in any order. For example: PSA plus adjuvant; PSA-TCSA-CSA; CSA-TCSA-PSA; TCSA-PSA-TCSA-CSA; TCSA-CSA-TCSA-PSA; PSA-TCSA-CSA-TCSA; CSA-TCSA-PSA-TCSA; PSA-TCSA-TCSA-CSA; TCSA-PSA-CSA-TCSA; TCSA-CSA-PSA-TCSA; and combination thereof, any of which may be repeated a number of times. Composite epitopes include but are not limited to composites of different combination of epitopes including repeated epitopes. For example, the T cell stimulating portion may be between, on one side or the other, or on both sides of two different or the same epitopes. Preferably the antigen is a immunogenic peptide. Also preferably, the sequences of the peptide are contiguous and not individual components of the same composition. Antigens may contain an epitope specific to one or more pathogens. The immunogenic peptide/composition preferably contains a mimotope that mimics the structure of one or more epitopes of the same or a different pathogen. Mimotopes may differ from the epitope from which they are derived, preferably by 1, 2, 3, 4 or more amino acid sequences. Mimotopes may be derived from the same region of the same antigen of the same organism as the epitope and genetically differ from the epitope by strain, serotypes, species or isolate, wherein, for example, the various genetic regions differ by 1, 2, 3, or 4 amino acid sequences. The sequence of the mimotope epitope differs from the conserved region of each strain or serotype of the pathogen. Preferably the epitope comprises a single epitope and the mimotope comprises a single mimotope and the epitope and mimotope are contiguous.

A preferred adjuvant formulation comprises Freund's adjuvant, a liposome, saponin, lipid A, squalene, unilamellar liposomes having a liposome bilayer that comprises at least one phosphatidylcholine (PC) and/or phosphatidylglycerol (PG), as phospholipids, which may be dimyristoyl phosphatidylcholine (DMPC), dipalmitoyl phosphatidylcholine (DPPC), distearyl phosphatidylcholine (DSPC), dimyristoyl phosphatidylglycerol (DMPG), dipalmitoyl phosphatidylglycerol (DPPG), and/or distearyl phosphatidylglycerol (DSPG), a cholesterol, a monophosphoryl lipid A (MPLA), and a saponin. Preferred adjuvants also include, for example, AS01 (Adjuvant System 01) which is a liposome-based adjuvant which comprises QS-21 (a saponin fraction extracted from *Quillaja saponaria* Molina), and 3-O-desacyl-4'-monophosphoryl lipid A (MPL; a non-toxic derivative of the lipopolysaccharide from *Salmonella minnesota*) and on occasion a ligand such as a toll-like receptor (e.g., TLR4), AS01b which is a component of the adjuvant Shingrix, ALF (Army Liposome Formulation) which comprises liposomes containing saturated phospholipids, cholesterol, and/or monophosphoryl lipid A (MPLA) as an immunostimulant. ALF has a safety and a strong potency. AS01 is included in the malaria vaccine RTS,S (Mosquirix). ALF modifications and derivatives include, for example, ALF adsorbed to aluminum hydroxide (ALFA), ALF containing QS21 saponin (ALFQ), and ALFQ adsorbed to aluminum hydroxide (ALFQA). Composition of the disclosure may include one or more pharmaceutically acceptable carriers.

Epitopes and mimotopes that are generally considered to generate a protective immune response against a microbial pathogen include epitopes and mimotopes obtained or derived from gram positive bacteria, gram negative bacteria, fungi including neoantigens and cryptic antigens. Epitopes that are generally considered to generate an immune response specific to cell wall material include, for example, epitopes and mimotopes that are specific to glycoprotein, polysaccharides are bound to cell wall, N-acetylglucosamine, cell wall polymers, hydroxyproline-rich glycoproteins (HRGP), alpha crystallin domain (ACD), arabinogalactan proteins (AGP), glycine-rich proteins (GRPs), proline-rich proteins (PRP), peptidoglycan (PGN), pseudo-peptidoglycan, LTA, LPS and derivatives and combinations thereof. Epitopes that are generally considered to generate an immune response is a T cell stimulating epitope include, for example, epitopes of tetanus toxin, tetanus toxin heavy chain proteins, diphtheria toxoid (e.g., natural and recombinant forms of CRM), tetanus toxoid, *Pseudomonas* exoprotein A, *Pseudomonas aeruginosa* toxoid, *Bordetella pertussis* toxoid, *Clostridium perfringens* toxoid, *Escherichia coli* heat-labile toxin B subunit, *Neisseria meningitidis* outer membrane complex, Hemophilus influenzae protein D, Flagellin Fli C, Horseshoe crab Haemocyanin, and fragments, derivatives, and modifications thereof including both natural and recombinant forms.

Another embodiment of the invention is directed to immunogenic compositions comprising antigens that are useful to treat or preferably prevent infection and disease associated with one or more pathogens including but not limited to bacteria, viruses, parasites, fungi or a combination thereof. These immunogenic compositions may be vaccines, either of which may include pharmaceutically acceptable components.

Another embodiment of the invention is directed to antibodies that are specifically reactive to the immunogenic peptides/antigens disclosed herein. Antibodies may be polyclonal or monoclonal derived from a mammal or may be non-human and thereafter humanized. Preferred antibodies are opsonic. The invention includes hybridomas that produce the monoclonal antibodies.

Another embodiment of the invention is directed to methods of prevention and/or treatment comprising the antibodies described herein that are specifically reactive to one or more pathogenic organisms. Antibodies may be polyclonal or monoclonal derived from a mammal or may be non-human and thereafter humanized. Preferred antibodies are opsonic and/or neutralize toxicity. The invention includes hybridomas that produce the monoclonal antibodies.

Another embodiment of the invention is directed to polynucleotides that encode composite antigens of the invention include vectors containing these polynucleotides, vectors including expression vectors and recombinantly engineered organisms containing integrated nucleic acid sequences as disclosed herein.

Another embodiment of the invention is directed to methods for generating an immune response against one or more pathogens in a mammal comprising administering to the mammal the antigen or antibodies of this disclosure. Preferably, the immune response generated or as administered is protective against one or more different strains, serotypes or species of organisms and prevents or reduces inflammation.

Other embodiments and advantages of the invention are set forth in part in the description, which follows, and in part, may be obvious from this description, or may be learned from the practice of the invention.

DESCRIPTION OF THE DRAWINGS

FIG. 8 Monoclonal antibody production with TB Pep 01 and TB Pep 02.

FIG. 14 Opsonophagocytic killing of live *M. smegmatis* by the anti-TB Pep01 MABs—LD7 and CA6 using the macrophage cell line U-937.

DESCRIPTION OF THE INVENTION

Figure 1:
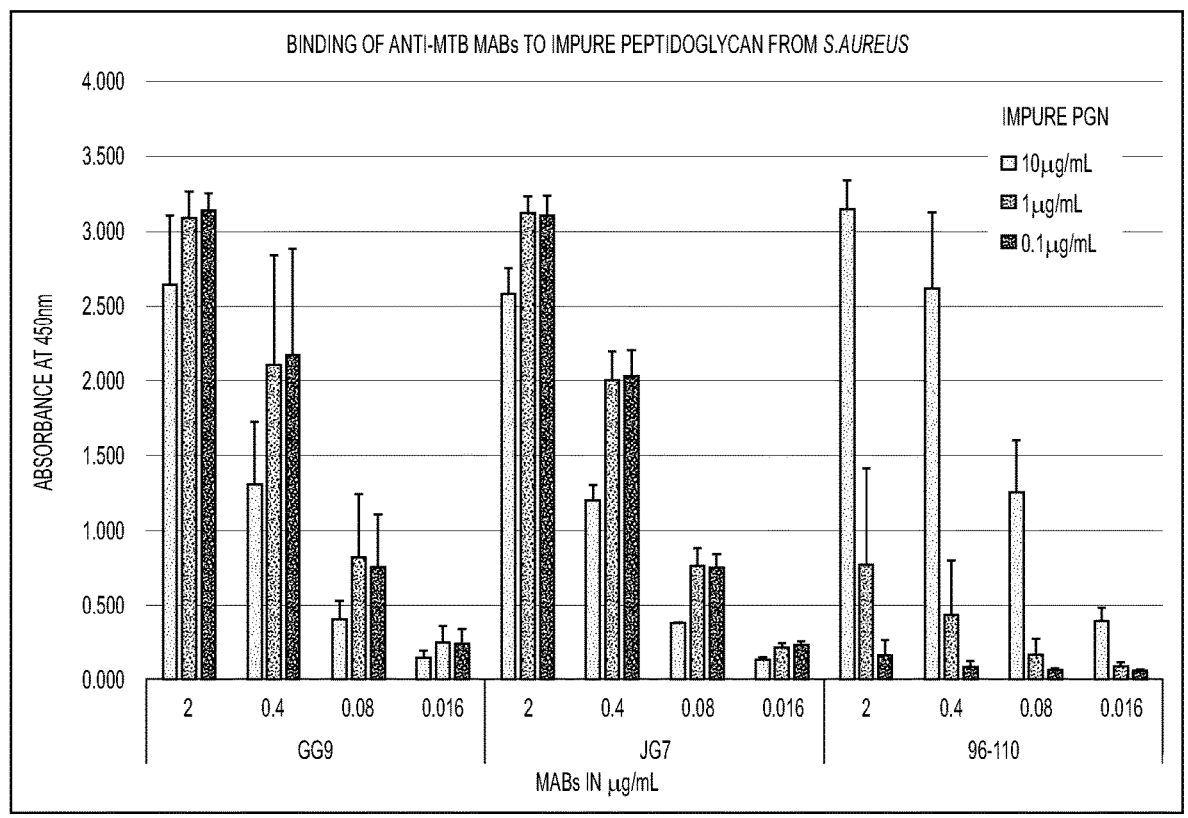
FIG. 1 Binding of anti-MTB MABs JG7 and GG9, and an anti-LTA MAB (96-110) to cell wall mixture (unpurified cell wall) as screened by ELISA.

Vaccinations and vaccines are often the best mechanism for avoiding an infection and preventing the spread of debilitating and dangerous pathogens. With respect to many different infections, vaccinations are often the only effective option as treatment options are few and those that are available provide only limited effectiveness. Conventional vaccinations require a priori understanding or general identification of the existing antigenic regions of the pathogen. The pathogen itself is propagated and a suitable vaccine developed from heat-killed or otherwise attenuated microorganisms. Alternatively, an antigen or collection of antigens is identified that will generate a protective immune response upon administration. The need for a vaccine is especially urgent with respect to preventing infection by bacteria, viruses, and parasites. Many such pathogens and especially certain viruses mutate constantly often rendering the vaccine developed to the prior or originating pathogen useless against the new strains that emerge. As a consequence, vaccines against infections are reformulated yearly and often administered at fairly high doses. The manufacturing costs are high and administering vaccines against pose a great many complications and associated risks to patients.

Septic shock is a common cause of death in patients in intensive care units and is caused by bacterial cell wall components to include but is not limited to, for example, PGN and LTA of gram-positive bacteria, and for example, LPS of gram-negative bacteria. These bacteria alone or in combination can invade the bloodstream or release cell wall components into the bloodstream and tissues causing shock and multi-organ failure. Cell wall components may act synergistically to induce cytokines and chemokines that cause over production of the inflammatory response and promote tissue damage and shock.

It has been surprisingly discovered that an effective immunogenic composition and/or vaccine can be produced from antigens constructed basically as disclosed and described herein. Immunogenic antigens as disclosed herein contain two or more epitopes or one or more epitopes plus one or more mimotopes, any of which may be a composite epitope. Epitopes and mimotopes are obtained or derived from an antigenic region of a pathogen or of multiple pathogens that generate an immunological response. Preferably, the plurality includes one or more epitopes that generate an immunological response to cell wall material and a mimotope that generates an immunological response to the same or a different pathogen. In the present disclosure, a mimotope comprises a macromolecule that mimics the structure of an epitope. Because of this property it causes an immunological response such as an antibody response similar to the one elicited by the epitope being mimicked. Similarity as measured by the strength of the immunological response (e.g., a cellular response, an antibody response) generated is preferable at least 50%, at least 60%, at least 70%, at least 80%, at least 90%, at least 95% or more. Basically, a mimotope mimics an epitope sequence with a different structure that retains the immunogenic properties of the native epitope structure. Preferably, the mimotope is a peptide sequence and differs from the epitope being mimicked by 1, 2, 3, 4, or more amino acids. Alternatively, the mimotope may not be a peptide but a different macromolecule such as, for example, a saccharide, a polysaccharide, a lipid, a fatty acid, peptide nucleic acid (PNA), or a combination of macromolecules. Preferably, the antigen contains one or more epitopes that stimulate the generation of an immunological response such as, for example, a T cell response. As an alternative to a T cell stimulating epitope, or in addition to the T cell stimulating epitope, the immunogenic peptide/composition may also include an adjuvant. Immunogenic antigens of the invention may contain one or more epitopes that represent a combination of conserved regions of two or more epitopes. Composite epitopes can be combinations of two or more conserved sequences that have different amino acid sequences by adding one or more amino acids from one sequence to the one or more other peptide sequences, so that the composite epitope sequence is a combination of sequences and is longer and different from any of the individual peptide sequences. Such combined epitopes are referred to herein as composite epitopes. Peptides that contain multiple different epitopes or mimotopes that are not normally found together are referred to herein as composite peptides. Composite peptides have two or more contiguous epitope sequences, two or more contiguous mimotope sequences, two or more composite epitope sequences, one or more contiguous epitope sequences coupled to one or more mimotopes or composite epitopes, one or more mimotopes coupled to one or more epitopes or composite epitopes, or any combination thereof. Composite antigens are similar to composite peptides but all epitopes do not necessarily reside of a contiguous sequence. Composite peptides and antigens as disclosed herein may contain a plurality of immunologically responsive regions not normally connected to each other or found together that are obtained or derived from one or multiple sources (e.g., virus particles, parasites, bacteria, fungi, cells). These immunological regions are preferably amino acid sequences or epitopes that are representative of sequences found at those antigenic regions of a pathogen or other antigen associated with an infection or a disease or, importantly, associated with stimulation of the immune system to provide protection against the pathogen.

The immunogenic peptides/compositions as disclosed herein are useful to treat or prevent the infection, and in addition to reduce or prevent over production of an inflammatory response, tissue damage, and septic shock. Administration of a composition comprising monoclonal antibodies specific to a pathogen plus antibodies to cell wall material promotes opsonization and modulation or down regulation of inflammation. One way to measure down regulation of inflammation is for instance to show the up regulation of Interleukin-10 (IL-10), an immunomodulatory cytokine with potent anti-inflammatory properties and down regulation of IL-12 that strongly promotes inflammation.

Epitopes and mimotopes that generate a protective immune response against a microbial pathogen(s) include epitopes and mimotopes obtained or derived from gram positive bacteria, gram negative bacteria, parasites, viruses, and fungi including neoantigens and cryptic antigens of any pathogen. Bacterial pathogens include, for example, *Bacillus* spp. (e.g., *Bacillus anthracis*), *Mycobacteria* spp. (e.g., *M. tuberculosis, M. smegmatis, M. leprae*), *Escherichia* spp. (e.g., *E. coli*), *Staphylococcus* spp. (e.g., *S. aureus*), *Pneumococcus* spp. (e.g.,), *Streptococcus* spp. (e.g., *S. pneumoniae, S. mutans, S. pyogenes, S. anginosis, S. sanguinis, S. dysgalactiae*), *Vibrio* spp. (e.g., *V. cholera*), *Haemophilus* spp. (e.g., *H. influenzae*), *Pseudomonas* spp. (e.g., *P. aeruginosa*), and *Yersinia* spp. (e.g., *Y. pestis*).

Epitopes and mimotopes that generate an immune response specific to cell wall material include, for example, epitopes that are specific to glycoprotein, capsule, N-acetylglucosamine, cell wall polymers, hydroxyproline-rich glycoproteins (HRGP), alpha crystallin domain (ACD) of heat shock and other proteins, arabinogalactan proteins (AGP), glycine-rich proteins (GRPs), proline-rich proteins (PRP), peptidoglycan (PGN), heat shock protein (HS), lipoarabinomannan (LAM), pseudopeptidoglycan, lipoteichoic acid (LTA), lipopolysaccharide (LPS), and derivatives and combinations thereof. Epitopes and mimotopes that generate an immune response specific to viral material include, for example, epitopes and mimotopes that are specific to influenza virus proteins such as HA (hemagglutinin), NA (neuraminidase), M2e (matrix protein 2 ectodomain), HEF (Hemagglutinin-Esterase-Fusion), or CM2 (second membrane protein).

Epitopes and mimotopes that generate an immune response is a T cell stimulating epitope include, for example, epitopes and mimotopes of tetanus toxin, tetanus toxin heavy chain proteins, diphtheria toxoid (e.g., natural and recombinant forms of CRM {cross-reactive material} such as CRM197), tetanus toxoid, *Pseudomonas* exoprotein A, *Pseudomonas aeruginosa* toxoid, *Bordetella pertussis* toxoid, *Clostridium perfringens* toxoid, *Escherichia coli* heat-labile toxin B subunit, *Neisseria meningitidis* outer membrane complex, Hemophilus influenzae protein D, Flagellin Fli C, Horseshoe crab Haemocyanin, and fragments, derivatives, and modifications thereof including both natural and recombinant forms. Data bases of immune system epitopes include, for example, MHCBN (Major Histocompatability Binding predictions): A database of MHC/TAP binder and T-cell epitopes; BCIPEP: A database of B-cell epitopes; SYFPEITHI—online database of T cell epitopes; IEDB (Immune Epitope Data Base)—Database of T and B cell epitopes with annotation of recognition context; ANTI-JEN—T and B cell epitope database at the Jenner institute, UK; IMGT/3Dstructure-DB—Three-dimensional structures of B and T cell epitopes with annotation of IG and TR, Montpellier, France; SEDB: A Structural Epitope Database—Pondicheery University, and Epitopes at the US National Library of Medicine Medical Subject Headings (MeSH).

One embodiment of the invention is directed to immunogenic antigens and compositions that contain two or more epitopes, which may include composites; one or more epitope and one or more mimotope, which may include composites; or one or more mimotopes. Mimotopes are amino acid sequences that do not exist in nature and are otherwise artificially constructed that have a different structure that the epitope being mimicked but produce the same or a similar immunological response. These epitopes and mimotopes are artificially arranged and preferably along a single amino acid sequence or peptide. The plurality may contain multiples of the same epitope and/or mimotope, although not in a naturally occurring order, or multiples of a variety of different epitopes and mimotopes from one or more pathogens. Epitopes may be identical to known immunological regions of a pathogen. Epitopes and mimotopes may be entirely new constructs that have not previously existed and are artificially constructed such as by chemical synthesis or recombinant engineering. Preferably, the immunogenic antigens of the invention also contain regions that induce a B cell and/or T cell response such as, for example, a killer T-cell ($T_C$ or CTL) response, a helper T-cell ($T_H$) response, and/or a memory T cell response (Tm) or preferably a opsonophagocytic response. Peptides also contain one or more epitopes and mimotopes of immunologically responsive regions of, for example, cell wall material, of the same or a different pathogenic organism. Immunological responsive regions of cell wall materials include, for example but not limited to, amino acid sequences that are epitopes of PGN, LTA, LAM, heat shock protein, and LPS.

Preferred epitope combinations (any of which may be mimotopes or composite epitopes) along a single peptide sequence include, for example, Acr-LAM-LTA; LAM-T cell-LAM; NA-LAM; HA-HA-NA-Acr; M2e-Acr; M2e-T cell; HA-HA-NA; HA-HA-NA-Acr; T cell-HA-HA-NA; M2e-NA; PDG-Acr; PDG-LAM-LTA; Acr-PDG-HS; ACD-LAM-LTA; LAM-LTA-ACD; Acr-PDG-LAM; LAM-LAM-LTA; LTA-LAM-PDG. These epitope combinations may further include a T cell epitope at the amino terminus, at the carboxy terminus, and/or in between other epitopes, and compositions may include an adjuvant.

Preferably the sequence of the immunogenic antigen comprises antigenic determinants in the epitopes and mimotopes that are specific to one or more pathogens (e.g., pathogen-specific antigen; PSA; cell surface antigen; CSA; virus-specific antigen; VSA), and one or more T cell stimulating antigens (T cell stimulating antigen; TCSA). Preferably, the antigen contains a combination of an epitope that is generally protective against a microbial pathogen, at least one epitope that is specific to PGN or LTA from gram-positive bacteria, or LPS from gram-negative bacteria, and CRM. Epitopes and mimotopes include but are not limited to composites of combination of PSA, TCSA and CSA. For example, the T cell stimulating portion may be between, on one side or the other, or on both sides of two different epitopes. Preferred structures include: TCSA1-CSA-2-TCSA2, etc. various combinations and multiples thereof.

These vaccines and antibodies provide a dual action by both up modulating an inflammatory response to promote OPKA, while binding cell PGN and LTA fragments from dead and damaged bacteria (and live bacteria) thus down regulating cytokines that induced septic shock and produce an over reactive inflammatory response. In effect, the PGN and LTA fragments are absorbed by the antibodies which, acting synergistically, are like a sponge removing these toxic materials from a mammalian system Eliminating or mitigating the effects of cell wall PGN and LTA provides an important prophylaxis and treatment for bacterial infections and septic shock.

An immunogenic antigen is preferably an engineered, artificially created antigen made from two or more different epitopes, one or more epitopes plus one or more mimotopes, or one or more mimotope, such that the resulting composite antigen has physical and/or chemical properties that differ from or are additive or synergistic of the individual constituent epitopes. Preferable the antigen, when exposed to the immune system of a mammal, is capable of simultaneously generating an immunological response to the constituent epitope and preferably to a greater degree (e.g., as measurable from a cellular or humoral response to an identified pathogen) than the individual constituent epitopes. In addition, the immunogenic antigen provides the added function of generating a protective immunological response in a patient when used as a vaccine and against the pathogens(s) from each of the constituent epitopes. Preferably, the immunogenic antigen has the additional function of providing protection against not only the pathogens from which the constituents were derived, but related pathogens as well. These related pathogenic organisms may be strains or serotypes of the same species of organism, or different species of the same genus of organism, or different organisms entirely that are only related by a common epitope.

Isolated epitopes and mimotopes are regions obtained or derived from a protein or peptide of a pathogen, so that the composite, that elicits a robust immunological response when administered to a mammal. Preferably, that robust response provides the mammal with an immunological protection against developing disease from exposure to the pathogen. Preferably each epitope and mimotope of the composite contains about 20 or less amino acids, preferably about 15 or less amino acids, preferably about 10 or less amino acids, preferably about 8 or less amino acids, preferably about 6 or less amino acids, and also preferably about 4 or less amino acids.

A composite antigen may be created from two or more epitopes and mimotopes, such that the resulting composite has physical and/or chemical properties that differ from or are additive of the constituent epitopes and is generally longer than any one of the constituent epitopes. Preferable the composite, when exposed to the immune system of a mammal, is capable of simultaneously generating an immunological response to each of the constituent epitopes and mimotopes of the composite and preferably to a greater degree than that achieved by either of the constituent epitopes and/or mimotopes individually. In addition, the composite provides the added function of generating a protective immunological response in a patient when used as a vaccine and against the pathogen(s) of each of the constituent epitopes. Preferably, the composite has the additional function of providing protection against not only the pathogens from which the constituents were derived, but related pathogens as well. These related pathogenic organisms may be strains or serotypes of the same species of organism, or different species of the same genus of organism, or different organisms entirely that are only related by a common epitope.

Immunogenic and composite antigens of the invention are entirely artificial molecules that do not otherwise exist in nature and to which an immune system has not been otherwise exposed. Preferably, composites are formed or derived from conserved immunological regions that are combined on a single sequence or mixed so that the composite represents immunologically responsive regions of proteins and/or polypeptides that are highly conserved between related pathogens. Although a vaccine can be developed from a single composite, in many instances the most effective vaccine may be developed from multiple, different composites and may include adding a natural protein such as cell surface/wall antigens (e.g. PGN) or antigens conjugated to a T cell stimulating antigen (e.g. CRM) to the composite peptides (with or without adjuvant) to create a mixture that is not found in nature.

Accordingly, immunogenic antigens and compositions as disclosed herein may contain two or more different epitopes, one or more epitopes plus one or more mimotopes, or one or more mimotopes, to provide an effective vaccine. Although such immunogenic antigens preferably comprise one or more composite epitopes and/or mimotopes, the immunological response achieved from a vaccination with an immunogenic antigen or group of antigens of this disclosure, provides protection against infection caused by the original strains from which the sequence of the antigen was originally obtained or derived, and also provides immunological protection against other strains, serotypes and/or species that share one or more of the general conserved regions represented in the antigen. Thus, the resulting immune response achieved from a vaccination with an antigen is more broadly protective than can be achieved from a conventional single antigen vaccination against multiple strains, serotypes, and species or otherwise related pathogens regardless of antigenic drift that may take place in the evolution of the pathogen. Preferably, vaccines developed from immunogenic antigens of the invention avoid any need for repeated or annual vaccinations, the associated complications and expenses of manufacture, and the elevated risks to the patient. These vaccines are useful to treat individuals and populations, thereby preventing infection, mortality and pandemics, and are useful to compliment conventional vaccines.

As discussed herein, the immunogenic antigen preferably comprises a single chain of amino acids with sequences derived from two or more epitopes, one or more epitopes plus one or more mimotopes, or one or more mimotopes of epitopes of pathogenic microorganisms, that may be the same pathogen of the one of more epitopes or different. Epitope sequences may be repeated consecutively and uninterrupted along a composite sequence or interspersed among other sequences that may be single or a few amino acids as spacers or sequences that encode peptides (collectively spacers) and may be immunogenic. Preferably the antigen is immunogenic and capable of inducing a cellular (T cell) or humoral (B cell) immune response in a mammal. Peptides sequence from unrelated microbes may be combined into a single composite antigen. For example, viral sequences of selected immunoresponsive peptides may be interspersed with conserved sequences or epitopes selected from other microbes, such as, for example, bacteria such as *S. pneumococcus, P. auriginosa* or *S. aureus*.

Preferably the antigen comprises a single contiguous amino acid sequence of about 65 amino acids or less, about 60 amino acids or less, about 55 amino acids or less, about 50 amino acids or less, about 45 amino acids or less, about 40 amino acids or less, about 35 amino acids or less, about 30 amino acids or less, or about 25 amino acids or less. The advantages of having all epitopes on a single sequence include but are not limited to at least: (i) the ease of manufacture of a single peptide compared to the manufacture of multiple peptides; (ii) the standardization achieved by having a single peptide against the same or against multiple pathogens; (iii) the absence of a need to coordinate the mixture and administration of multiple peptides; and (iv) the ease by which a vaccine of one peptide can be administered. These advantages not only improve the speed by which a vaccine can be manufacture and the speed by which a vaccine can be distributed, but such vaccine can save lives.

The epitopes, mimotopes, composite epitopes, and combinations thereof of the immunogenic antigen may be of any sequence and size, but is preferable composed of natural amino acids and is more than 5 but less than 35 amino acids in length, preferably less than 30, preferably between 5 and 25 amino acids in length, preferably between 8 and 20 amino acids in length, and more preferably between 5 and 15 amino acids in length. Composite antigens preferably contain any number of composite and/or other epitopes. The most effective number of epitopes of a composite antigen against a particular pathogen, pathogen family, or group of pathogens may be determined by one skilled in the art from the disclosures of this application and using routine testing procedures. Immunogenic antigens may be effective with one epitope, composite or otherwise, preferably with 2 or more, 3 or more 4 or more, 5 or more, 6 or more, 7 or more, 8 or more, 9 or more, 10 or more, or greater amino acids sequences. Optionally, immunogenic antigens may include one or more spacers between epitopes which may be sequences of antigenic regions derived from the same or from one or more different pathogens, or sequences that serve as immunological primers or that otherwise provide a boost to the immune system. That boost may be generated from a sequence of amino acids that are known to stimulate the immune system, either directly or in association with one or more T cell stimulating epitopes and/or one or more adjuvants.

In one preferred embodiment, immunogenic antigens useful to generate an immunological response against gram positive microorganisms such as *Staphylococcal* spp. (e.g., *S. aureus, S. epidermidis* and methicillin-resistant *Staphylococcus aureus* (MRSA)) or *Streptococcus* spp. comprise epitopes LTA or PNG, and/or new epitopes derived from similar structures.

Also preferred are immunogenic antigens containing epitopes, composite epitopes, and/or mimotopes of surface or cell wall proteins of gram-positive microorganisms such as *Staphylococci* or *Mycobacterium* spp. such as *M. tuberculosis* and *M. smegmatis* and *Clostridium* spp. such as *C. tetani*, and gram-negative bacteria such as *E. coli* and *Pseudomonas* that contain epitopes, composite epitopes, and/or mimotopes of LPS, and/or new immunological sites derived from similar structures.

Another embodiment of the invention is directed to a contiguous sequence of one or more epitopes, one or more composite epitopes, and/or one or more mimotopes, which may comprise a sequence that does not exist naturally and must be artificially constructed. Preferably, a contiguous sequence of the invention contains one or more epitopes, one or more composite epitopes, and/or one or more mimotopes, which may be a combination of sequences from conserved regions of a pathogen that are common to or differ within multiple pathogens. For example, where two pathogens contain similar conserved regions that differ by only a single amino acid, the composite may comprise an epitope identical to one conserved region and a mimotope of the other conserved region.

It is also preferable that an immunogenic antigen of the disclosure contains a plurality of repeated epitopes, composite epitopes, and/or mimotopes and, optionally, linker regions between or surrounding each epitope, composite or otherwise, and the plurality of epitopes and mimotopes can be of the same or different regions. Preferred linkers include amino acid sequences of antigenic regions of the same or of different pathogens, or amino acids sequences that aid in the generation of an immune response. Preferred examples include, but are not limited to, any of the various antigenic regions of bacteria such as, but not limited to *Mycobacteria*, such as *M. tuberculosis, Streptococcus*, such as *S. pneumococcus, Staphylococcus* such as *S. aureus*. Preferred examples include, but are not limited to, any of the various antigenic regions of viruses such as, but not limited to Respiratory viruses such as, for example, influenza virus, respiratory syncytial virus, corona virus, parainfluenza virus, adenovirus, rhinovirus, human metapneumovirus, and enterovirus, or pathogenic viruses such as, for example, Adenovirus, Zika virus, Rubella virus, Hepatitis virus, Herpes Simplex virus, retrovirus, varicella zoster virus, human papilloma virus, parvovirus, human metapneumovirus and enterovirus, and HIV. Parasitic organisms from which composite antigens of the disclosure may be developed include, for example, *Plasmodium* spp., *Leishmania* spp., *Guardia* spp., endoparasites, protozoan, and helminth spp. Fungal organisms include, for example, *Cryptococci, aspergillus*, and *candida*. It is also preferred that composite antigens contain epitopes that generate a T cell response, a B cell response, an OPKA response, or a combination in conjunction with a specific response to the pathogen. Diseases caused by treated or prevented with composite antigens of the disclosure include sepsis, colds, flu, gastrointestinal infections, sexually transmitted diseases, immunodeficiency syndrome, nosocomial infections, Celiac disease, inflammatory bowel disease, inflammation, multiple sclerosis, auto-immune disorders, chronic fatigue syndrome, Rheumatoid arthritis, myasthenia gravis, Systemic lupus erythematosus, and infectious psoriasis.

Another embodiment of the invention is directed to methods of immunizing mammals with the immunogenic antigens of this disclosure. Antisera obtained from the immunized mammals are reactive against the pathogens from which the composite antigen was derived. Another embodiment of the invention is therefore antisera obtained from the immunized mammals, which may be further purified for testing or utilized therapeutically for administration to another mammal and thereby provides protection against infection from the one or more pathogens. It is also preferred that the antisera obtained provide a broad protection, not just against the pathogens from which the immunogenic antigen was derived, but also from additional pathogens that may differ by strain, serotype, or even species.

Another embodiment of the invention is directed to vaccines composed of the immunogenic antigens or antisera developed from the immunogenic antigens of the invention. Preferably, the vaccines of the invention are less susceptible to variation of antigenicity due to antigenic shift of pathogens which reduces or eliminates the need for annual or repeated vaccination to maintain protection of patient populations against potential outbreaks of infection from new viral isolates. In addition, the vaccines of the invention generally and advantageously provide increased safety considerations, both in their manufacture and administration (due in part to a substantially decreased need for repeated administration), a relatively long shelf life in part due to minimized need to reformulate due to strain-specific shift and drift, an ability to target immune responses with high specificity for particular microbial epitopes, and an ability to prepare a single vaccine that is effective against multiple pathogens, each of which may be a different but know strain or species of the same pathogen. The invention encompasses antigenic and antibody compositions, methods of making such compositions, and methods for their use in the prevention, treatment, management, and/or prophylaxis of an infection. The compositions disclosed herein, as well as methods employing them, find particular use in the treatment or prevention of viral, bacterial, parasitic and/or fungal pathogenesis and infection using immunogenic compositions and methods superior to conventional treatments presently available in the art. Antibodies of this disclose include bi-valent antibodies that are specifically reactive against two different epitopes, one epitope that is specific for each arm of the antibody.

Another embodiment of the invention is directed to methods of preventing or controlling infection, such as, for example, an outbreak of viral, parasitic, fungal or bacterial infection, preferably but not limited to a MTB, *Staphylococcal* infections, Influenza infections, corona virus infections, and others. The method includes at least the step of providing an immunologically effective amount of one or more of the disclosed immunogenic compositions, antisera and/or antibodies to a susceptible or an at-risk member of the population, for a time sufficient to prevent, reduce, lessen, alleviate, control, or delay the outbreak of such an infection in the general population.

Another embodiment of the invention is directed to methods for producing a protective immune response against infection in a mammal in need thereof. Such a method generally includes a step of providing to a mammal in need thereof, an immunologically effective amount of one or more of the immunogenic compositions disclosed herein under conditions and for a time sufficient to produce such a protective immune response against one or more species, strains, or serotypes of an infectious organism. Additionally, the invention also provides a method for administering a prophylactic antiviral or antimicrobial composition such as antisera or antibodies to at least a first cell, tissue, organ, or organ system in a mammal that generally involves providing to such a mammal a prophylactically effective amount of at least a first immunogenic composition as disclosed herein.

Another embodiment of the invention is directed to an immunogenic composition comprising the composite antigens of the invention having one or more repeated peptide sequences, or fragments, variants, or derivatives of such peptide sequences that are conserved across a plurality of proteins in the same or different pathogen. The conserved regions from which the composite sequence is derived may be conserved within subtypes of the same pathogen or different pathogens. Preferred pathogens include, but are not limited to bacteria, viruses, parasites, fungi and viruses.

Immunogenic antigens of the disclosure may also be obtained or derived from the sequences of bacteria (e.g., epitope combinations, mimotopes, composites) such as, for example, multiple or combined epitopes of the proteins and/or polypeptides of, for example, but not limited to *Streptococcus, Pseudomonas, Mycobacterium* such as *M. tuberculosis, Shigella, Campylobacter, Salmonella, Haemophilus influenza, Chlamydophila pneumonia, Corynebacterium diphtheriae, Clostridium tetani, Mycoplasma pneumonia, Staphylococcus aureus, Moraxella catarrhalis, Legionella pneumophila, Bordetella pertussis, Escherichia coli*, such as *E. coli* 0157, and multiple or combined epitopes, mimotopes, and/or composites of conserved regions of any of the foregoing. Exemplary parasites from which sequences may be obtained or derived include but are not limited to *Plasmodium* such as *Plasmodium falciparum* and *Trypanosoma*. Exemplary fungi include but are not limited to *Aspergillus fumigatus* or *Aspergillus flavus*.

Preferably subtypes of a pathogen and/or strains within a subtype are at least about 80 percent, at least about 90 percent, at least about 95 percent, at least about 96 percent, at least about 97 percent, at least about 98 percent, or at least about 99 percent identical. Certain subtypes may be closer to 100 percent identical (invariant). Preferably, at least one peptide sequence within the composite antigen is also conserved on homologous proteins (e.g., protein subunits) of at least two bacterial particles.

The disclosure provides a immunogenic peptide or polypeptide that includes at least one antigen, which comprises one or more epitope, composite epitopes, and/or mimotope sequences which may be conserved across a plurality of homologous proteins that are conserved in a population of viral or bacterial strains or serotypes, and a pharmaceutically acceptable carrier. In exemplary immunogenic antigens, sequences from one or more proteins and or one or more microbes may be included in the immunogenic antigen. In other embodiments, one or more epitope, one or more composite epitopes, and/or one or more mimotope sequences may be repeated one, or more times. Preferably the epitope and/or mimotope sequences as presented in the immunogenic peptide sequence provide immune recognition of the native protein of the organism from which they were selected as well as other bacterial, or viral strains, or serotypes. In all embodiments disclosed, compositions may include a T cell epitope, formulated with an adjuvant and a pharmaceutically acceptable carrier.

The immunogenic antigen may include one or more T-cell stimulating epitopes, such as diphtheria toxoid, tetanus toxoid, a polysaccharide, a lipoprotein, or a derivative or any combination thereof (including fragments or variants thereof). Typically, the at least one repeated sequence of the composite antigen is contained within the same molecule as the T-cell stimulating epitopes. In the case of protein-based T-cell stimulating epitopes, the at least one repeated sequence of the composite antigen may be contained within the same polypeptide as the T-cell stimulating epitopes or may be associated in other ways. Preferably, at least one repeated sequence is incorporated within or alongside the one or more T-cell stimulating epitopes in a composite antigen of the invention.

Immunogenic antigens of the invention may be synthesizing by in vitro chemical synthesis, solid-phase protein synthesis, and in vitro (cell-free) protein translation, or recombinantly engineered and expressed in bacterial cells, fungi, insect cells, mammalian cells, virus particles, yeast, and the like.

A preferred immunogenic antigen includes at least one of the following elements: highly conserved epitope and mimotope sequences; a T cell epitope; a polysaccharide; a polynucleotide; a structural component; or a combination or multiple thereof. The at least one structural component may include one or more of: at least one linker segment; at least one sugar-binding moiety; at least one nucleotide-binding moiety; at least one protein-binding moiety; at least one enzymatic moiety; or a combination thereof. The invention encompasses methods of preparing an immunogenic composition, preferably a pharmaceutical composition, more preferably a vaccine, wherein a target antigen of the present invention is associated with a pharmaceutically acceptable diluent, excipient, or carrier, and may be used with most any adjuvant. Preferred pharmaceutically acceptable components include, for example, water, a fatty acid, a saccharide, a polysaccharide, an oil, an ester, a lipid, glycol, polyethylene glycol (PEG), a diluent, an excipient, a bulking agent, a colorant, or a combination thereof. Preferred adjuvants include, for example, AS01 (Adjuvant System 01) which is a liposome-based adjuvant which comprises QS-21 (a saponin fraction extracted from *Quillaja saponaria* Molina), and 3-O-desacyl-4'-monophosphoryl lipid A (MPL; a non-toxic derivative of the lipopolysaccharide from *Salmonella minnesota*) and on occasion a ligand such as a toll-like receptor (e.g., TLR4), AS01b which is a component of the adjuvant Shingrix, ALF (Army Liposome Formulation) which comprises liposomes containing saturated phospholipids, cholesterol, and/or monophosphoryl lipid A (MPLA) as an immunostimulant. ALF has a safety and a strong potency. AS01 is included in the malaria vaccine RTS,S (Mosquirix). ALF modifications and derivatives include, for example, ALF adsorbed to aluminum hydroxide (ALFA), ALF containing QS21 saponin (ALFQ), and ALFQ adsorbed to aluminum hydroxide (ALFQA). A preferred adjuvant formulation comprises Freund's adjuvant, a liposome, saponin, lipid A, squalene, unilamellar liposomes having a liposome bilayer that comprises at least one phosphatidylcholine (PC) and/or phosphatidylglycerol (PG), as phospholipids, which may be dimyristoyl phosphatidylcholine (DMPC), dipalmitoyl phosphatidylcholine (DPPC), distearyl phosphatidylcholine (DSPC), dimyristoyl phosphatidylglycerol (DMPG), dipalmitoyl phosphatidylglycerol (DPPG), and/or distearyl phosphatidylglycerol (DSPG), a cholesterol, a monophosphoryl lipid A (MPLA), and a saponin. Preferably the mole ratio of the cholesterol to the phospholipids is greater than about 50:50 and also that the unilamellar liposomes have a median diameter size in micrometer range as detected by light scattering analysis. Additional preferred adjuvants are disclosed in U.S. Pat. No. 10,434,167 (by Carl R. Alving et al.) which issued Oct. 8, 2019, the entirety of which is incorporated by reference herein.

Within the context of the present invention, that a relatively small number of conservative or neutral substitutions (e.g., 1 or 2) may be made within the epitope, composite or mimotope sequence of the immunogenic antigen disclosed herein, without substantially altering the immunological response to the peptide. In some cases, the substitution of one or more amino acids in a particular peptide may in fact serve to enhance or otherwise improve the ability of the peptide to elicit an immune or T-cell response in an animal that has been provided with a composition that comprises the modified peptide, or a polynucleotide that encodes the peptide. Suitable substitutions may generally be identified using computer programs and the effect of such substitutions may be confirmed based on the reactivity of the modified peptide with antisera and/or T-cells. Accordingly, within certain preferred embodiments, a peptide for use in the disclosed diagnostic and therapeutic methods may comprise a primary amino acid sequence in which one or more amino acid residues are substituted by one or more replacement amino acids, such that the ability of the modified peptide to react with antigen-specific antisera and/or T-cell lines or clones is not significantly less than that for the unmodified peptide.

As described above, preferred peptide variants are those that contain one or more conservative substitutions of an epitope which may also form a mimotope. A "conservative substitution" is one in which an amino acid is substituted for another amino acid that has similar properties, such that one skilled in the art of peptide chemistry would expect the secondary structure and hydropathic nature of the peptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Examples of amino acid substitutions that represent a conservative change include: (1) replacement of one or more Ala, Pro, Gly, Glu, Asp, Gln, Asn, Ser, or Thr; residues with one or more residues from the same group; (2) replacement of one or more Cys, Ser, Tyr, or Thr residues with one or more residues from the same group; (3) replacement of one or more Val, Ile, Leu, Met, Ala, or Phe residues with one or more residues from the same group; (4) replacement of one or more Lys, Arg, or His residues with one or more residues from the same group; and (5) replacement of one or more Phe, Tyr, Trp, or His residues with one or more residues from the same group. A variant may also, or alternatively, contain non-conservative changes, for example, by substituting one of the amino acid residues from group (1) with an amino acid residue from group (2), group (3), group (4), or group (5). Variants may also (or alternatively) be modified by, for example, the deletion or addition of amino acids that have minimal influence on the immunogenicity, secondary structure and hydropathic nature of the peptide.

Epitopes and mimotopes may be arranged in any order relative to one another in the composite antigen sequence. The number of spacer amino acids between two or more of the epitopic sequences can be of any practical range, including, for example, from 1 or 2 amino acids to 3, 4, 5, 6, 7, 8, 9, or even 10 or more amino acids between adjacent epitopes and mimotopes.

Another embodiment of the invention is directed to polynucleotides including DNA, RNA and PNA constructs that encode the antigenic sequences of the invention. These polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials. As is appreciated by those of ordinary skill in the art that, as a result of the degeneracy of the genetic code, there are many nucleotide sequences that encode a given primary amino acid sequence. Some of these polynucleotides bear minimal homology to the nucleotide sequence of any native gene. Nonetheless, polynucleotides that vary due to differences in codon usage are specifically contemplated by the present invention. Polynucleotides that encode an immunogenic peptide may generally be used for production of the peptide, in vitro or in vivo. Any polynucleotide may be further modified to increase stability in vivo. Possible modifications include, but are not limited to, the addition of flanking sequences at the 5' and/or 3'-ends; the use of phosphorothioate or 2'-o-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Another embodiment of the invention is directed to synthetic or recombinant nucleic acids as immunological compositions and vaccines that encode the immunogenic antigens of this disclosure and can be administered to be subsequently translated to immunogenic antigens that generate an immunogenic response to same pathogen or to multiple pathogens. Preferred pathogens that can be treated or prevented by nucleic acid vaccines of this disclosure include, but are not limited to bacterial, viral, parasitic, and fungal infections.

Another embodiment of the invention encompasses methods of vaccinating a subject against a pathogen that includes administering to a patient in need of vaccination a therapeutically or prophylactically effective amount of a vaccine, which vaccine includes an immunogenic antigen comprising one or more epitope, composite, mimotope, or other sequences, some of which may be conserved across a plurality of homologous proteins in a plurality of bacterial particles, and a pharmaceutically acceptable carrier, to provide a detectable immune response in the patient against the pathogen. Preferred pharmaceutically acceptable components include, for example, water, a fatty acid, a saccharide, a polysaccharide, an oil, an ester, a lipid, glycol, polyethylene glycol (PEG), a diluent, an excipient, a bulking agent, a colorant, or a combination thereof.

Another embodiment of the invention is directed to nucleotide or DNA vaccines encoding immunogenic antigens of the invention. A DNA vaccine of the invention contains the genetic sequence of the immunogenic antigen, plus other necessary sequences that provide for the expression of the composite antigen in cells. By injecting the mammal with the genetically engineered DNA, the immunogenic antigen is produced in or preferably on cells, which the mammal's immune system recognizes and thereby generates a humoral or cellular response to the antigen, and therefore the pathogen. DNA vaccines have a number of advantages over conventional vaccines, including the ability to induce a more general and complete immune response in the mammal. Accordingly, DNA vaccines can be used to protect a mammal against disease caused from many different pathogenic organisms of viral, bacterial, and parasitic origin as well as certain tumors.

DNA vaccines typically comprise a bacterial DNA contained that encodes the immunogenic antigen contained in vectors or plasmids that have been genetically modified to transcribe and translate the antigenic sequences into specific protein sequences derived from a pathogen. By way of example, the vaccine DNA is injected into the cells of the body, where the cellular machinery transcribed and translates the DNA into the composite antigen. Immunogenic antigens, being non-natural and unrecognized by the mammalian immune system, are processed by cells and the processed proteins, preferably the epitopes, displayed on cell surfaces. Upon recognition of these antigens as foreign, the mammal's immune system generates an appropriate immune response that protects the mammal from infection. In addition, DNA vaccine of the invention are preferably codon optimized for expression in the mammalian cells of interest, such as but not limited to mouse or human cells. In a preferred embodiment, codon optimization involves selecting a desired codon usage bias (the frequency of occurrence of synonymous codons in coding DNA) for the particular cell type so that the desired peptide sequence is expressed.

Another embodiment of the invention is directed to therapeutic and prophylactic agents in a pharmaceutically acceptable composition for administration to a cell or an animal, either alone, or in combination with one or more other modalities of prophylaxis and/or therapy. Therapeutic and prophylactic agents of the invention include immunogenic antigens which may include epitopes, mimotopes, composite epitopes, and combinations thereof, DNA vaccines of the invention, antibodies of the invention, and/or T cells primed or exposed to immunogenic antigens of the invention. The formulation of pharmaceutically acceptable excipients and carrier solutions is well known to those of ordinary skill in the art, as is the development of suitable dosing and treatment regimens for using the particular compositions described herein in a variety of treatment regimens.

The amount(s) of immunogenic composition(s) and the time needed for the administration of such immunogenic composition(s) will be within the purview of the ordinary-skilled artisan having benefit of the present teachings. The administration of a therapeutically effective, pharmaceutically effective, and/or prophylactically effective amount of the disclosed immunogenic compositions may be achieved by a single administration, such as for example, a single injection of a sufficient quantity of the delivered agent to provide the desired benefit to the patient undergoing such a procedure. Alternatively, in some circumstances, it may be desirable to provide multiple, or successive administrations of the immunogenic compositions, either over a relatively short, or even a relatively prolonged period of time, as may be determined by the medical practitioner overseeing the administration of such compositions to the selected individual.

The immunogenic compositions and vaccines of the present invention are preferably administered in a manner compatible with the dosage formulation, and in such an amount as will be prophylactically or therapeutically effective and preferably immunogenic. Administration may be intramuscular (IM), subcutaneous (SQ), intradermal, intranasal, intraperitoneal or another method known to those skilled in the art and appropriate for the composition. The quantity to be administered depends on the subject to be treated, including, e.g., the capacity of the patient's immune system to mount an immune response, and the degree of protection desired. Suitable dosage ranges may be on the order of several hundred micrograms (µg) of active ingredient per vaccination with a preferred range from about 0.1 µg to 2000 µg (even though higher amounts, such as, e.g., in the range of about 1 to about 10 mg are also contemplated), such as in the range from about 0.5 µg to 1000 µg, preferably in the range from about 1 µg to about 500 µg and especially in the range from about 10 µg to about 100 µg. Suitable regimens for initial administration and booster shots are also variable but are typified by an initial administration followed by optional but preferred subsequent inoculations or other periodic administrations.

In certain embodiments, the dose would consist of the range of about 1 µg to about 1 mg total protein or target antigen. In one exemplary embodiment, the vaccine dosage range is about 0.1 µg to about 10 mg. However, one may prefer to adjust dosage based on the amount of peptide delivered. In either case, these ranges are merely guidelines from which one of ordinary skill in the art may deviate according to conventional dosing techniques. Precise dosages may be determined by assessing the immunogenicity of the composite produced in the appropriate host so that an immunologically effective dose is delivered. An immunologically effective dose is one that stimulates the immune system of the patient to establish an immune response to the immunogenic composition or vaccine. Preferably, a level of immunological memory sufficient to provide long-term protection against disease caused by microbial infection is obtained. The immunogenic compositions or vaccines of the invention may be preferably formulated with an adjuvant. By "long-term" it is preferably meant over a period of time of at least about 6 months, over at least about 1 year, over at least about 2 to 5 or even at least about 2 to about 10 years or longer.

Another embodiment of the invention is directed to antibodies that are specific for the immunogenic antigens as described here and conservative variants thereof. Antibodies specific for these polypeptides are useful, e.g., in both diagnostic and therapeutic purposes, e.g., related to the activity, distribution, and expression of target polypeptides. Antibodies of the invention may be classes IgG, IgM, IgA, IgD or IgE and include, but are not limited to, polyclonal antibodies, monoclonal antibodies, multiple or single chain antibodies, including single chain Fv (sFv or scFv) antibodies in which a variable heavy and a variable light chain are joined together (directly or through a peptide linker) to form a continuous polypeptide, and humanized or chimeric antibodies.

Antibodies specific for the immunogenic peptides of the invention can be generated by methods well known in the art. Such antibodies can include, but are not limited to, polyclonal, monoclonal, chimeric, humanized, single chain, Fab fragments and fragments produced by an Fab expression library. Numerous methods for producing polyclonal and monoclonal antibodies are known to those of skill in the art, and can be adapted to produce antibodies specific for the polypeptides of the invention, and/or encoded by the polynucleotide sequences of the invention (see, e.g., Coligan Current Protocols in Immunology Wiley/Greene, NY; Paul (ed.) (1991); (1998) Fundamental Immunology Fourth Edition, Lippincott-Raven, Lippincott Williams & Wilkins; Harlow and Lane (1989) Antibodies: A Laboratory Manual, Cold Spring Harbor Press, NY, USA; Stites et al. (Eds.) Basic and Clinical Immunology (4th ed.) Lange Medical Publications, Los Altos, CA, USA and references cited therein; Goding, Monoclonal Antibodies: Principles and Practice (2d ed.) Academic Press, New York, NY, USA; 1986; and Kohler and Milstein (1975).

The following examples illustrate embodiments of the invention but should not be viewed as limiting the scope of the invention.

EXAMPLES

Example 1

Figure 2:
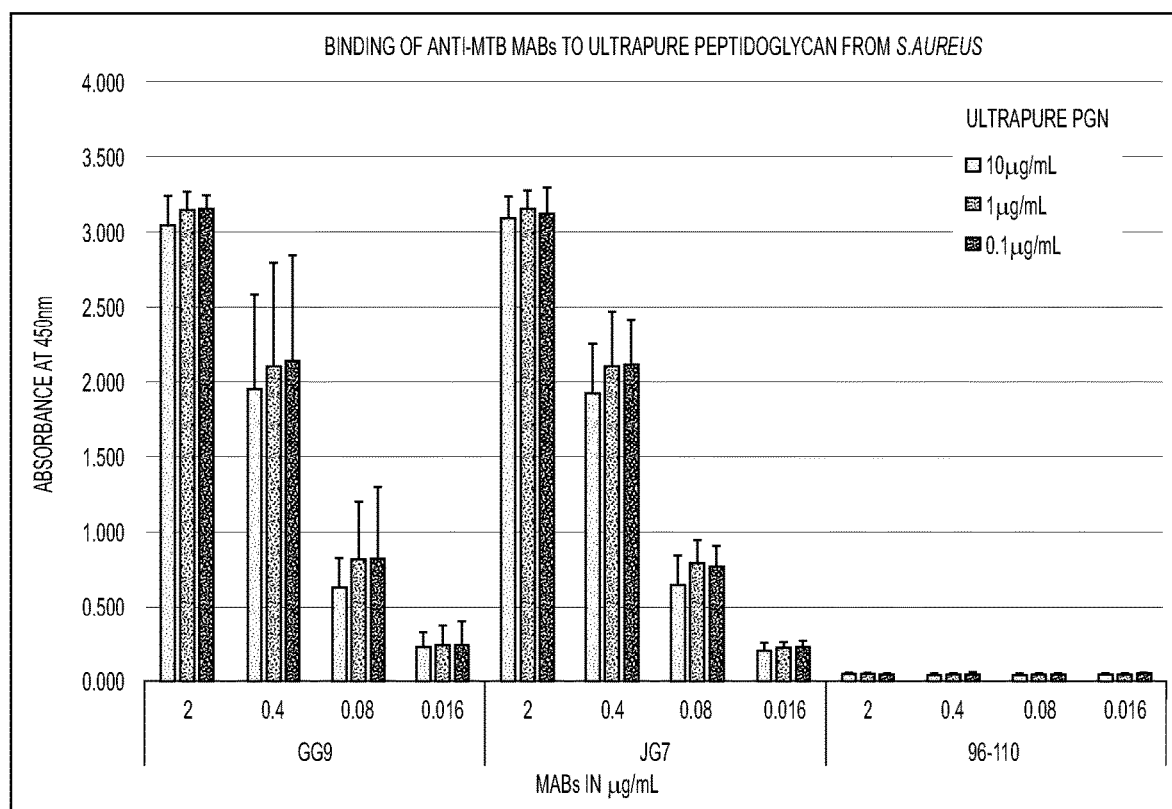
FIG. 2 Binding of anti-MTB MABs JG7 and GG9, and an anti-LTA MAB (96-110) to ultrapure PGN as screened by ELISA.

Two monoclonal antibodies (MABs) generated from mice immunized with ethanol-killed *Mycobacterium tuberculosis* (MTB) (anti-MTB MABs GG9 and JG7) and one anti-LTA MAB (96-110) were screened by Enzyme-Linked Immunosorbent Assay (ELISA) to determine recognition of cell wall antigens. Binding of MABs GG9, JG7 and 96-110 to a cell wall mixture and ultrapure PGN, both derived from *Staphylococcus aureus* was analyzed. MAB (96-110) directed against LTA only bound to the impure cell wall mixture that contained both LTA and PGN (FIG. 1) and not to the ultrapure PGN (that does not contain other cell wall components such as LTA) (FIG. 2), while anti-MTB MABs JG7 and GG9 bound to both the cell wall mixture and ultrapure PGN. Thus, antibodies specific for PGN and LTA can avidly bind each of the cell wall components (FIGS. 1 and 2).

Example 2

Figure 3:
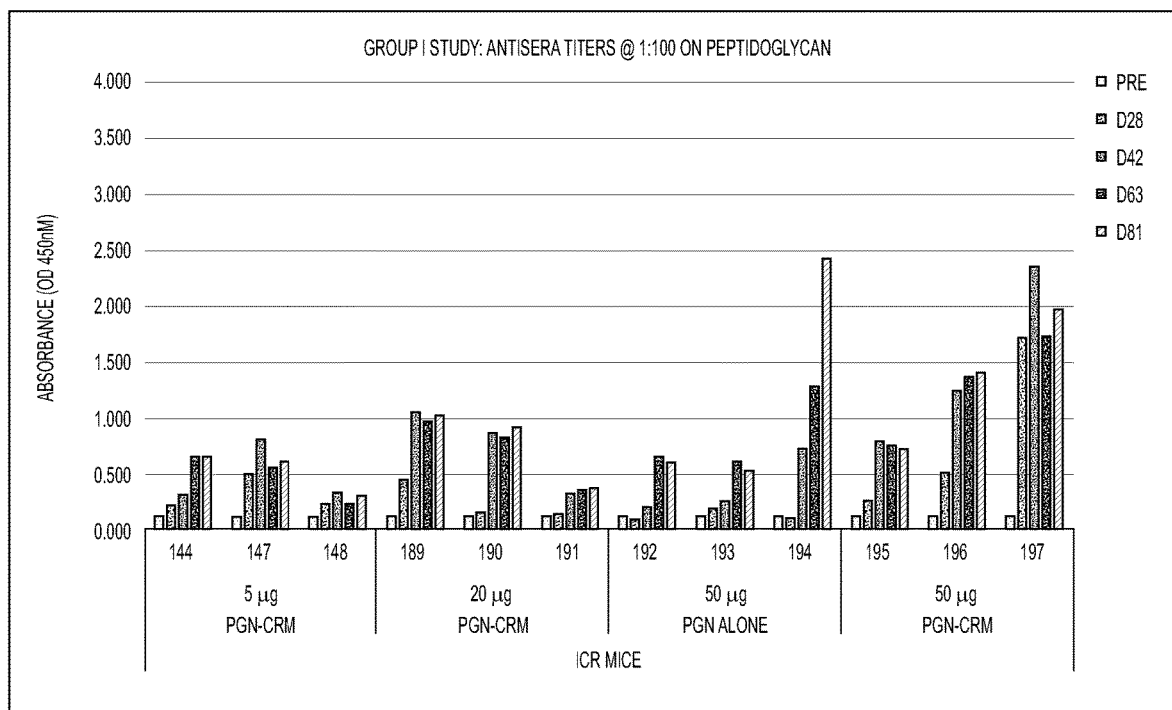
FIG. 3 Mice antisera titers on peptidoglycan as screened by ELISA whereby mice received PGN CRM-conjugated vaccine showed a more robust immune response by day 42 as compared to mice that received PGN only.
Figure 4:
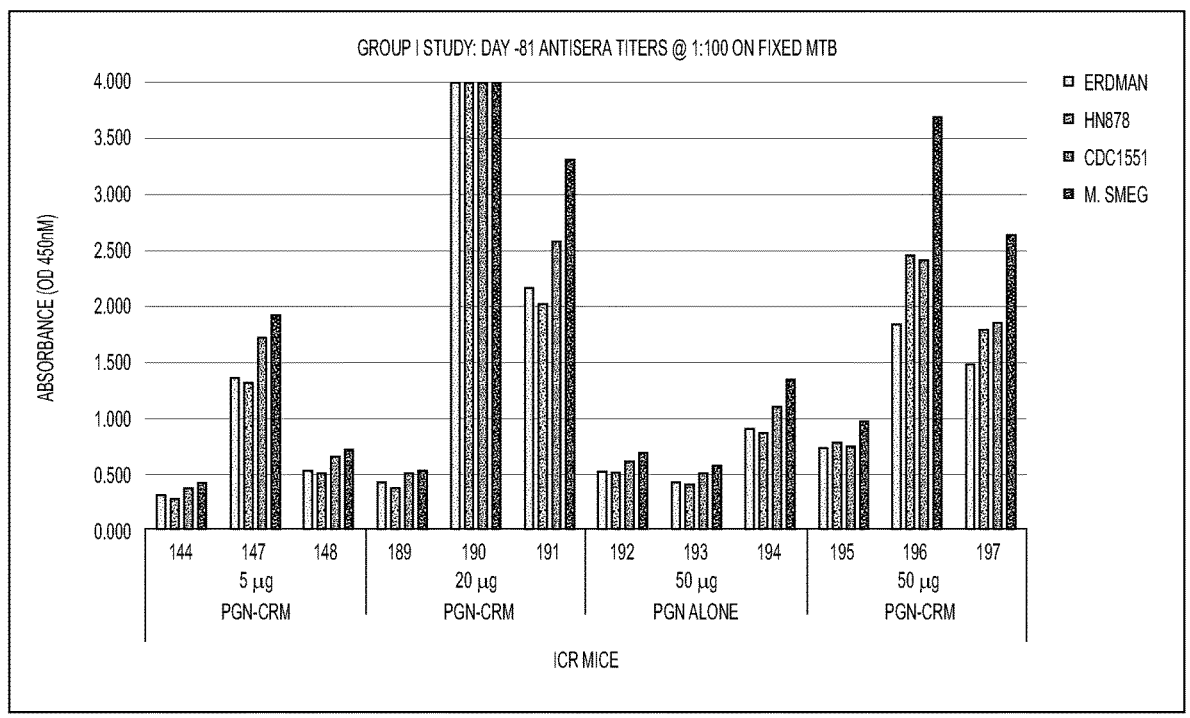
FIG. 4 Day-81 mice antisera titers on MTB and SMEG as screened by ELISA showing that MS 190 had the strongest immune response to MTB as compared to mice in other groups and a good candidate for fusion.
Figure 5:
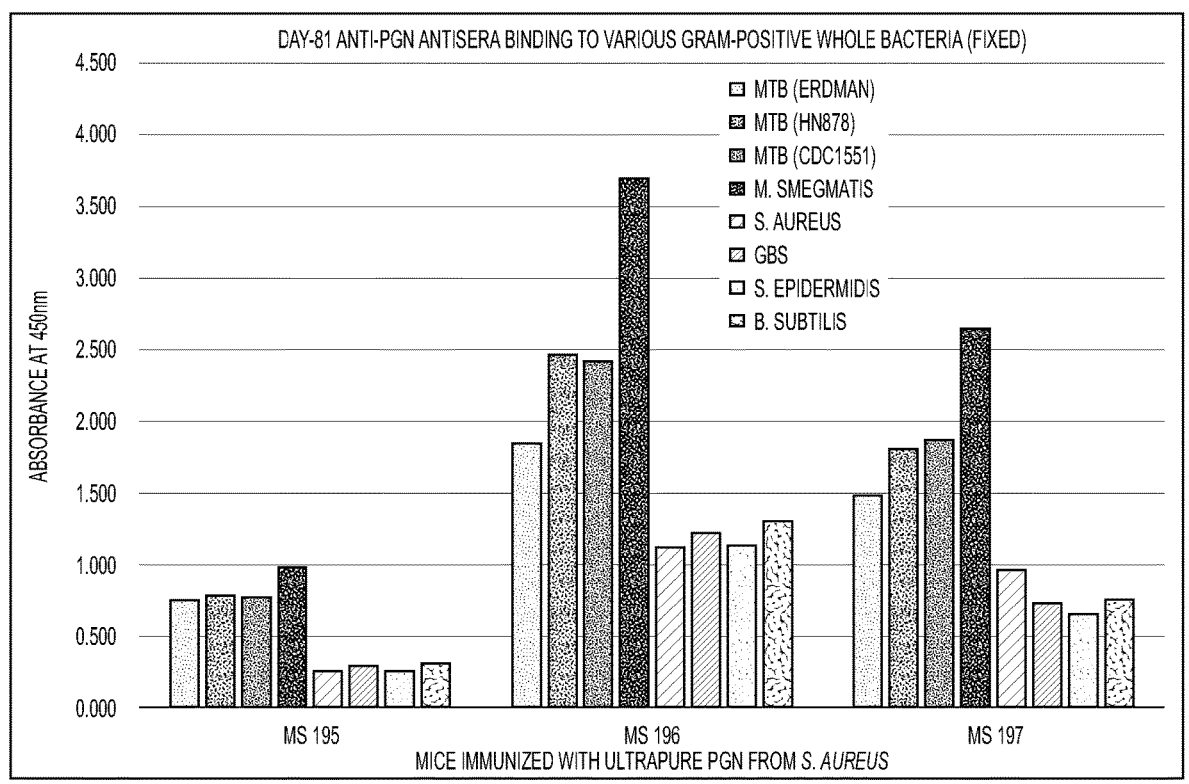
FIG. 5 Binding of day-81 anti-PGN serum antibodies from mice 195-197 to various gram-positive bacteria.

Female ICR mice were immunized subcutaneously with Ultrapure PGN, unconjugated or CRM-conjugated using three doses: 5, 20 and 50 µg/mouse and given with TiterMax Gold adjuvant (unconjugated PGN was only given at 50 µg). Booster immunizations were given on Days 20, 42 & 64 and retino-orbital bleeds were performed on Days 28, 42, 63 and 81. Antisera binding to PGN, MTB and various gram-positive bacteria were analyzed by ELISA. Unconjugated PGN was immunogenic in mice, but there was generally a more robust response in the conjugated groups compared to the unconjugated responses (FIG. 3). Strong immune responses to the cell wall component PGN and to several strains of MTB were detected and highest titers were evident from MS 190, 191, 196 & 197 (FIGS. 4 and 5). Thus, mice immunized with PGN alone or PGN-CRM conjugate vaccines develop a robust humoral response that demonstrated strong binding to PGN and bound to *Mycobacteria* to include MTB and *M. smegmatis* as well as other gram-positive bacteria, such as *S. aureus*, GBS, *S. epidermidis* and *B. subtilis*.

Example 3

Figure 6:
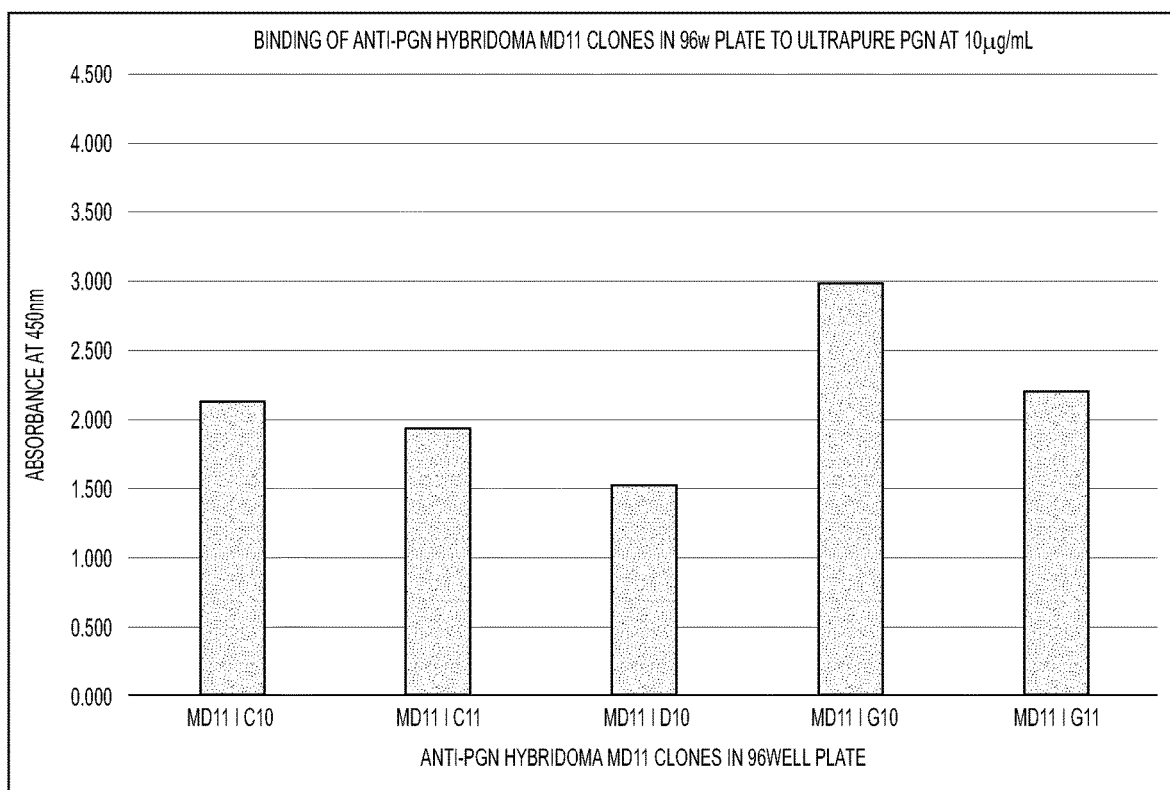
FIG. 6 Binding of anti-PGN hybridoma MD11 positive clones in 96 well plates on ultrapure PGN at 10 μg/mL FIG. 7 Binding of anti-PGN MD11 clones in 24 well plates on ultrapure PGN and various gram-positive bacteria.
Figure 7:
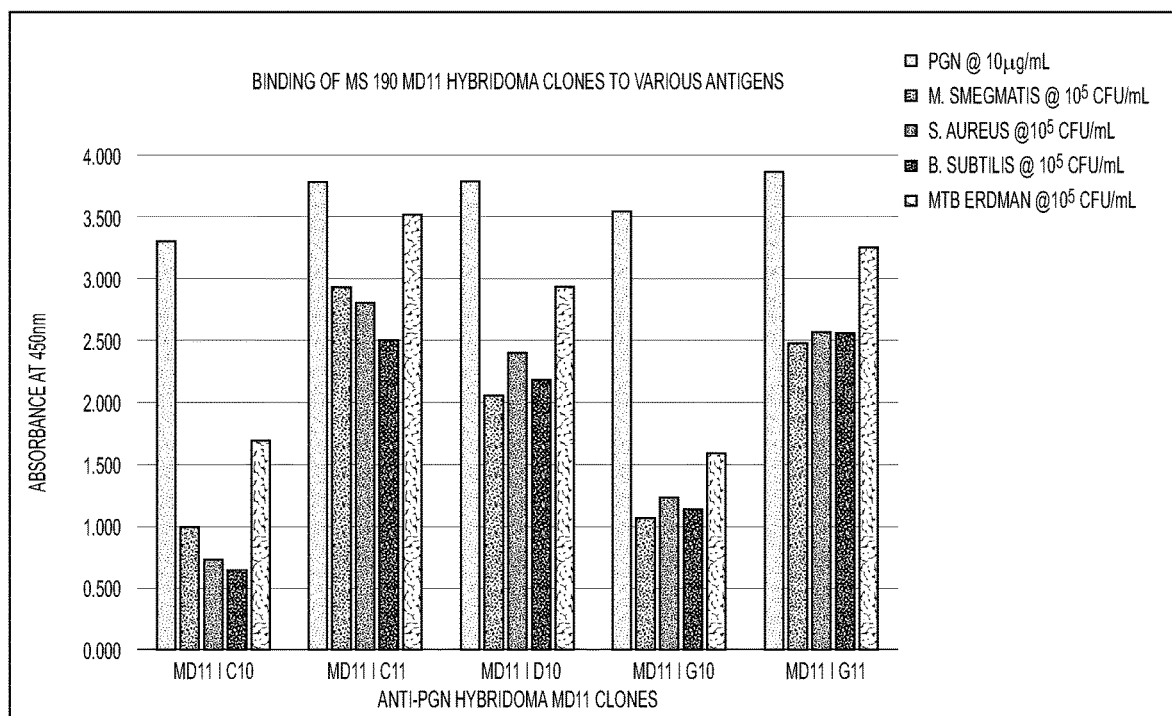

Immunization with PGN or LTA vaccines makes provision for the induction of humoral immunity and production of hybridomas that secrete anti-PGN and anti-LTA antibodies. Such antibodies, raised against cell wall components, can promote OPKA of bacteria and enhance clearance from the blood. Notably, from a group of ICR mice immunized with CRM-conjugated PGN (20 µg), mouse 190 elicited a strong immune response to PGN, MTB and other gram positive bacteria and led to its splenocytes being harvested and fused with myeloma cell line SP2/0 for the development of hybridoma MD11. Several anti-PGN positive clones (MD11) bound strongly to PGN (FIG. 6). These clones also showed strong binding to *Mycobacteria, S. aureus* and *B. subtilis* (FIG. 7). Supernatant collected from five hybridoma MD11 clones in 96 & 24-well culture plates bound to Ultrapure PGN, MTB, SMEG and other gram-positive bacteria (FIG. 5).

Example 4

A conserved epitope of the MTB alpha crystallin protein (Acr) was synthesized that induced mycobacterium binding antibodies. This protein is important for MTB survival in macrophages and long-term viability during latent, asymptomatic infections. A small conserved Acr epitope—SEFAYGSFVRTVSLPVGADE (SEQ ID No: 1; referred to as TB Pep 01) was identified.

A composite peptide was created combining TB Pep 01 and a conserved influenza HA and NA composite peptide (GNLFIAPWGVIHHPHYEECSCY; SEQ ID No: 25; influenza virus epitopes of HA, HA, and NA; referred to as TB Pep 02).

Figure 9:
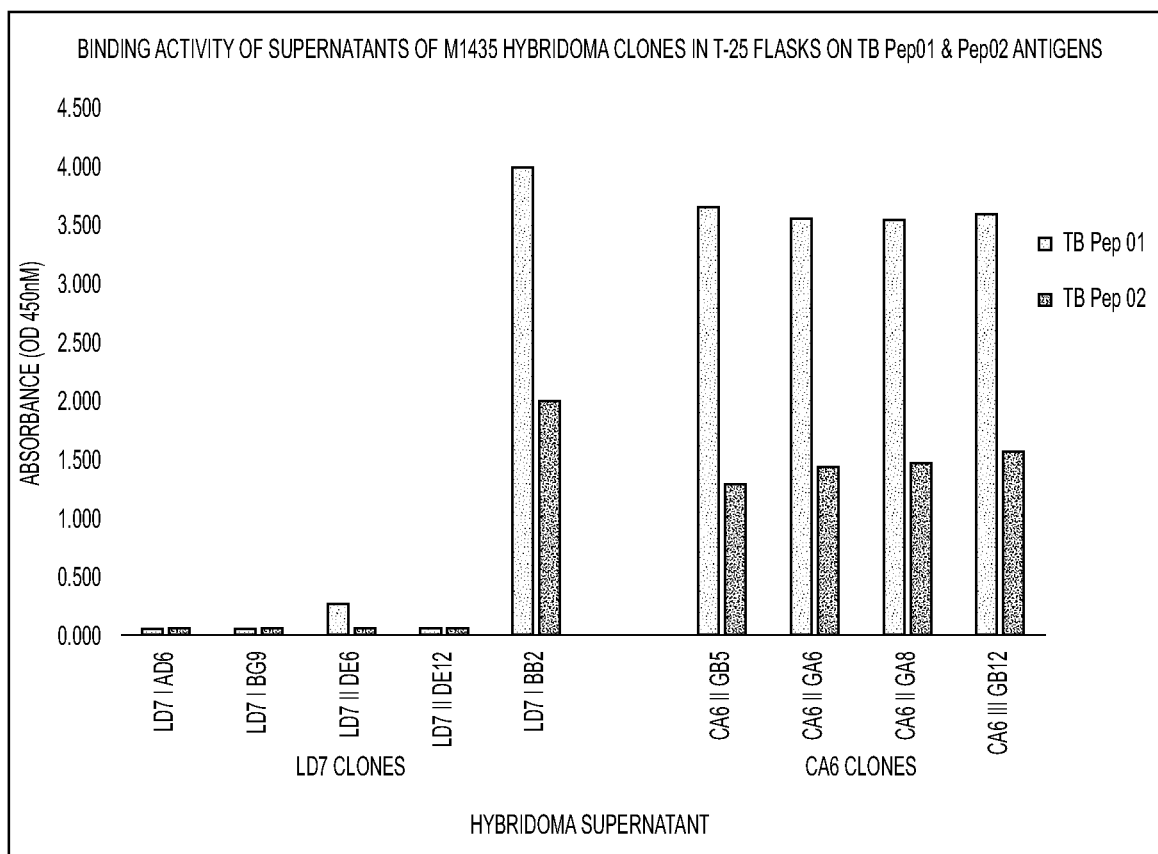
FIG. 9 Binding of supernatants from mouse M1435 derived hybridoma clones of LD7 and CA6 to various antigens.
Figure 10:
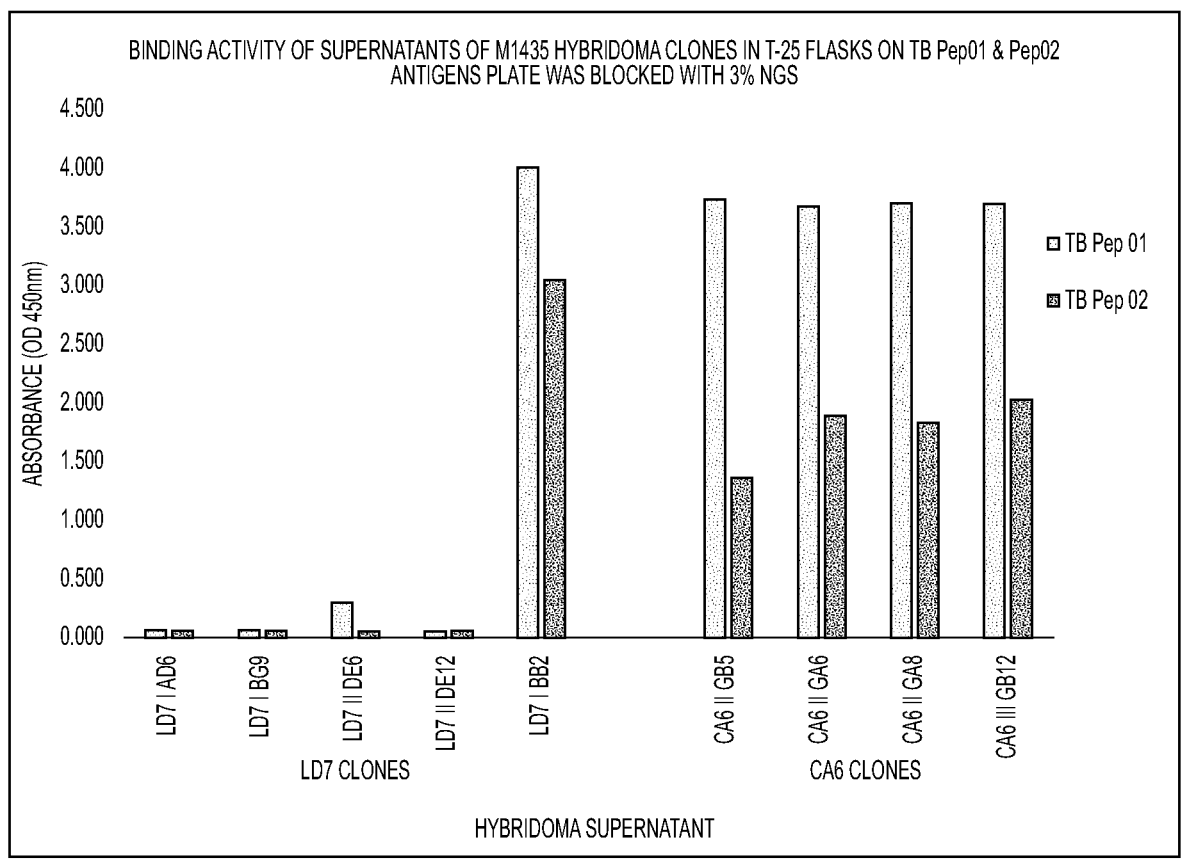
FIG. 10 Binding of supernatants from mouse M1435 derived hybridoma clones of LD7 and CA6 to various antigens with blocking with 3% NGS.
Figure 11:
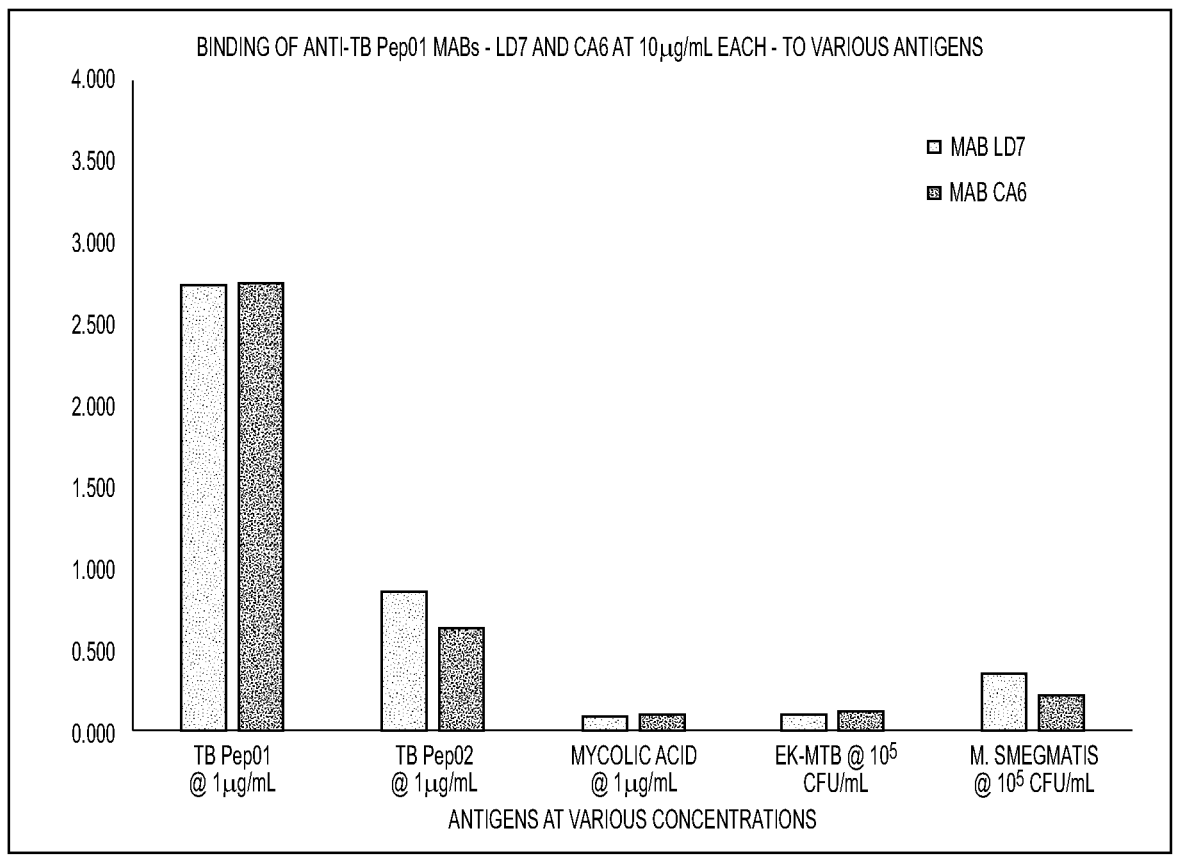
FIG. 11 Binding of anti-TB Pep 01 purified MABs LD7 I BB2 and CA6 II GA8 to fixed antigens.
Figure 12:
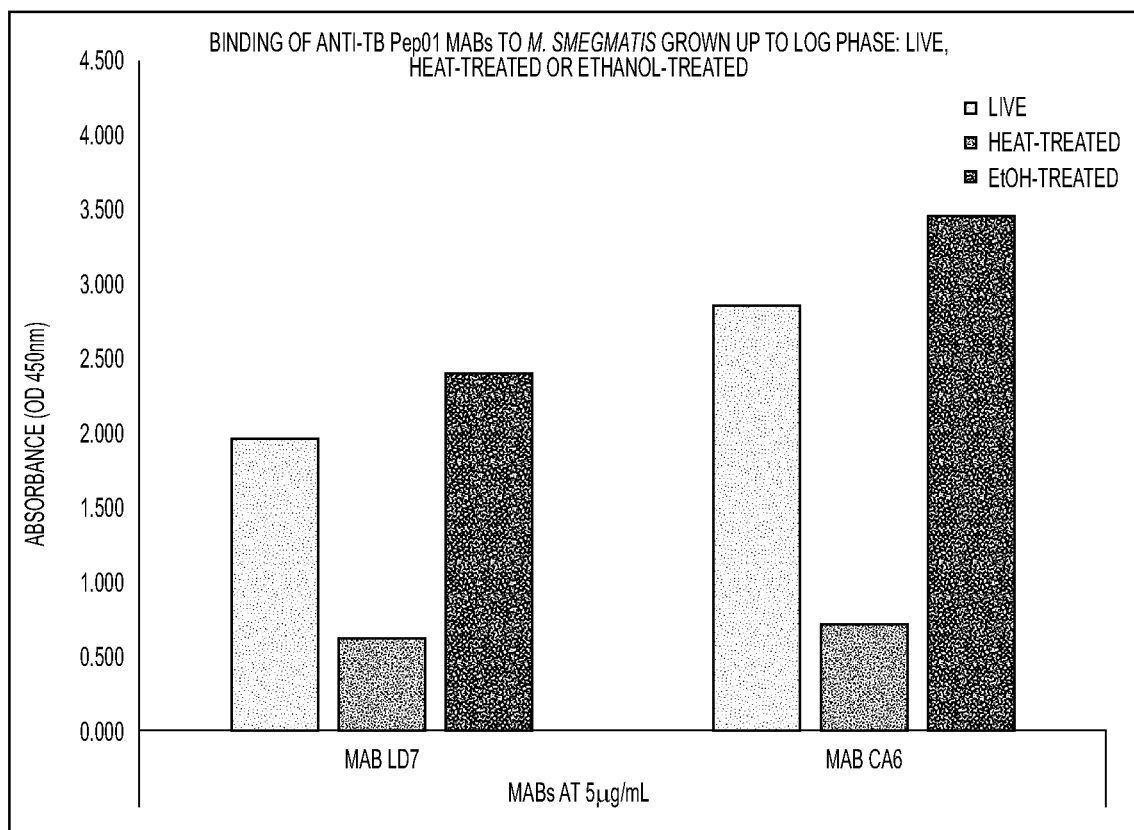
FIG. 12 Binding of anti-TB Pep 01 purified MABs LD7 and CA6 to live *M. smegmatis* at mid-Logarithmic phase (~10^7 CFU/mL).
Figure 13:
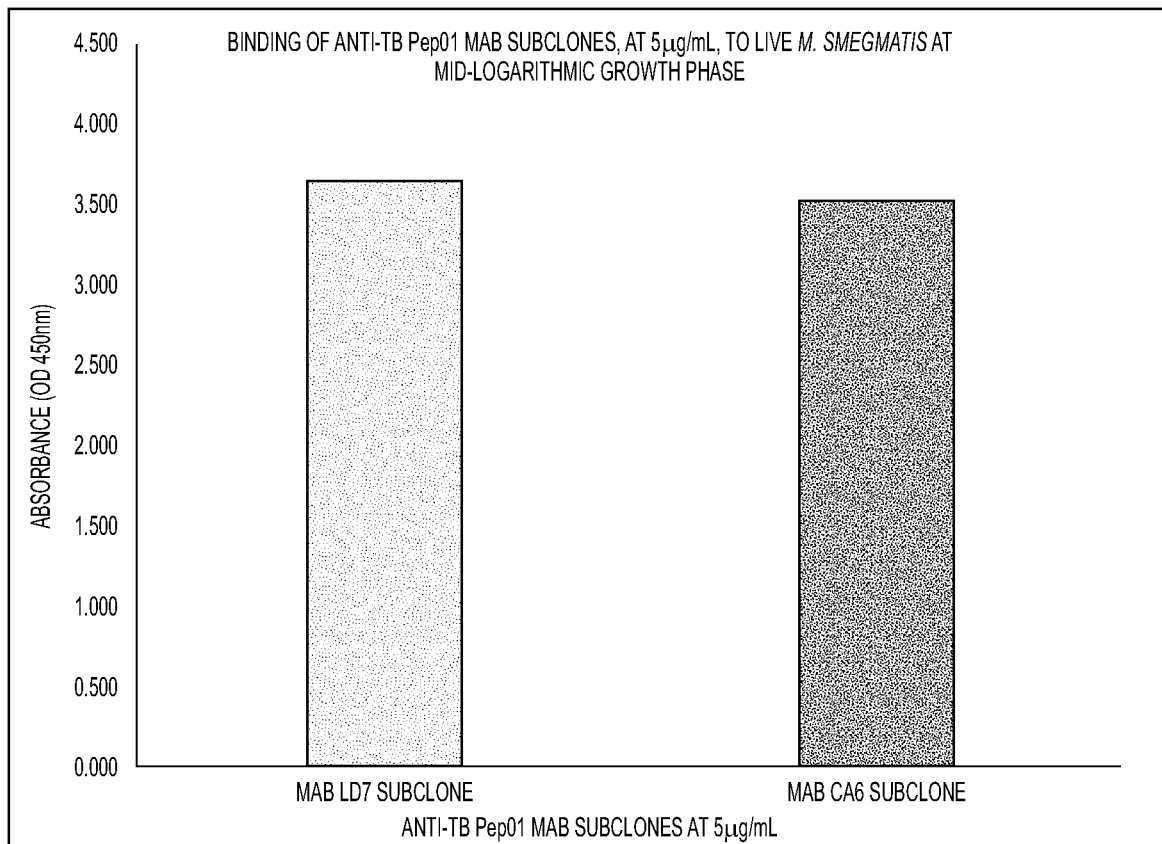
FIG. 13 Binding of anti-TB Pep01 purified MABs LD7 and CA6 to live *M. smegmatis* at mid-Logarithmic phase of growth.

Monoclonal antibodies (MABs) from mice immunized with this epitope bound to TB Pep 01 and TB Pep 02 (FIG. 8). Supernatants from mouse M1435 derived hybridoma clones of LD7 and CA6 bound to various antigens with and without 3% NGS (FIGS. 9 and 10). Anti-TB Pep 01 purified MABs LD7 I BB2 and CA6 II GA8 bound to certain fixed antigens (FIG. 11). Anti-TB Pep 01 purified MABs LD7 and CA6 bound to live *M. smegmatis* at mid-Logarithmic phase of growth (~10^7 CFU/mL). Conditions were live and heat-treated for 1 hr or ethanol treated for 1 hr (FIGS. 12 and 13). Binding of anti-TB Pep01 purified MABs LD7 and CA6 to live *M. smegmatis* at mid-Logarithmic phase of growth (FIG. 14). Opsonophagocytic killing of live *M. smegmatis* by the anti-TB Pep01 MABs—LD7 and CA6 was shown using the macrophage cell line U-937.

Mice immunized with TB Pep 01 CRM-conjugate induced antibodies that bound to the peptide and also bound to *Mycobacteria* such as *M. smegmatis* and induced OPKA for *M. smegmatis*.

Example 5

TB Pep01 is a peptide for the heat shock protein alpha-crystallin (hsp20) of MTB. Hsp20 is a family of proteins found across *Mycobacterium* including those nontuberculous species of the phylum actinobacteria, belonging to the genus *Mycobacterium*, e.g., *M. fortuitum*. See Ying Yuan, et al., "The 16-kDa a-crystallin (Acr) protein of *Mycobacterium tuberculosis* is required for growth in macrophages," Proc. Natl. Acad. Sci. USA 95:9578-9583, August 1998; incorporated by reference). There is an 80% homology of hsp20 (16 out of 20 amino acid) between *M. tuberculosis* and *M. smegmatis*, as shown below (Hsp20/alpha crystallin family protein with aa mismatches indicated as underlines):

SEFAYGSFVRTVSLPVGADE    SEQ ID No: 1
(Acr) *Mycobacterium tuberculosis*

SEFAYGSFMRSVTLPPGADE    SEQ ID No: 2
*Mycobacterium smegmatis*

SEFSYGSFVRTVSLPGGADE    SEQ ID No: 3
*Mycobacterium kansasii*

SEFSYGSFVRTVSLPAGADE    SEQ ID No: 4
*Mycobacterium mantenii*

SEFSYGSFVRTVTLPTDADE    SEQ ID No: 5
*Mycobacterium fortuitum*

SEFSYGSFARTVSLPAGANE    SEQ ID No: 6
*Mycobacterium xenopi*

Example 6

Composite peptide vaccines that include epitopes of cell wall PGN and LTA and induce antibodies that bind to the cell wall of live bacteria can promote OPKA of *Mycobacteria, Staphylococci* and other bacteria and enhance clearance from the blood. While LTA and PGN induce shock, antibodies that bind to cell wall components could provide important and useful strategies to prevent and/or treat shock in patients infected with *Mycobacteria, Staphylococci* and other bacteria. These vaccines and antibodies alone, or with other agents can prevent and/or treat bacterial infection and shock. Combining PGN and LTA epitopes allows induction of antibodies to a highly conserved structure present in many bacterial pathogens. The antibodies so produced are effective against a large number of bacteria. Exemplary sequences include:

SEQ ID No: 7 WRMYFSHRHAHLRSP (LTA epitope/mimotope that binds to opsonic MABs)

SEQ ID No: 8 WHWRHRIPLQLAAGR (LTA epitope/mimotope that binds to opsonic MABs)

SEQ ID No: 9 WRMYFSHRHAHLRSPQYIKANSKFIGITE (LTA mimotope plus T cell epitope)

SEQ ID No: 10 WHWRHRIPLQLAAGRQYIKANSKFIGITE (LTA mimotope plus T cell epitope)

SEQ ID No: 11 QYIKANSKFIGITEWRMYFSHRHAHLRSP (T cell epitope plus LTA mimotope)

SEQ ID No: 12 QYIKANSKFIGITEWHWRHRIPLQLAAGR (T cell epitope plus LTA mimotope)

SEQ ID No: 13 WRMYFSHRHAHLRSPQYIKANSKFIGITEWHWRHRIPLQLAAGR (LTA mimotope plus T cell epitope plus LTA mimotope)

SEQ ID No: 14 WRMYFSHRHAHLRSPWHWRHRIPLQLAAGR (LTA mimotope plus LTA mimotope)

SEQ ID No: 15 WHWRHRIPLQLAAGRWRMYFSHRHAHLRSP (LTA mimotope plus LTA mimotope)

SEQ ID No: 16 WRMYFSHRHAHLRSPWHWRHRIPLQLAAGRQYIKANSKFIGITE (LTA mimotope plus LTA mimotope plus T cell epitope)

SEQ ID No: 17 QYIKANSKFIGITEWRMYFSHRHAHLRSPWHWRHRIPLQLAAGR (T cell epitope plus LTA mimotope plus LTA mimotope)

SEQ ID No: 18 HSFKWLDSPRLR (LAM MTB mimotopes)

SEQ ID No: 19 ISLTEWSMWYRH (LAM MTB mimotopes)

SEQ ID No: 20 ISLTEWSMWYRHQYIKANSKFIGITEHSFKWLDSPRLR (LAM MTB mimotope plus T cell epitope plus LAM MTB mimotope)

SEQ ID No: 21 QYIKANSKFIGITEHYEECSCYHSFKWLDSPRLR (T cell epitope plus Influenza NA epitope plus LAM MTB mimotope)

SEQ ID No: 22 SEFAYGSFVRTVSLPVGADEHSFKWLDSPRLR (MTB alpha crystallin protein epitope)

SEQ ID No: 23 SEFAYGSFVRTVSLPVGADEHSFKWLDSPRLRQYIKANSKFIGITE (MTB alpha crystallin protein epitope plus T cell epitope)

SEQ ID No: 24 SEFAYGSFVRTVSLPVGADE (Acr epitope; TB Pep 01)

SEQ ID No: 25 GNLFIAPWGVIHHPHYEECSCY (Pep 11; influenza virus epitopes of HA, HA, and NA)

SEQ ID No: 26 SEFAYGSFVRTVSLPVGADEGNLFIAPWGVIHHPHYEECSCY (Acr epitope plus influenza virus epitopes of HA, HA, and NA; TB Pep 02)

SEQ ID No: 27 SLLTEVETPIRNEWGLLTEVETPIRQYIKANSKFIGITE (Pep 5906)

SEQ ID No: 28 GNLFIAPWGVIHHPHYEECSCYQYIKANSKFIGITE (Pep 11 plus T cell epitope; influenza virus epitopes of HA, HA, and NA; Pep 64)

SEQ ID No: 29 QYIKANSKFIGITEGNLFIAPWGVIHHPHYEECSCY (T cell epitope plus Pep 11; influenza virus epitopes of HA, HA, and NA; Pep 63)

Example 7

The SEQ ID No: 25 is an influenza composite antigen comprised of two HA composite sequences and a conserved epitope sequence from NA. Immunization of mice with this influenza composite antigen induced antibodies to the conserved epitopes that bind to the influenza A viruses across groups 1 and 2 and can be formulated with an influenza matrix composite peptide antigen that also contains a T cell epitope (SEQ ID No: 27). In addition, Pep 11 (SEQ ID No: 25) was synthesized with a T cell epitope on both the N and C terminus (Pep 63; SEQ ID No: 29 and Pep 64; SEQ ID No: 28). Immunization of ICR mice SQ with unconjugated Pep 11, or Pep 64 each formulated with Pep 5906 in Addavax induced strong anti-influenza and epitope specific serum antibodies for HA, NA and Matrix epitopes. Mice given 20 µg of either peptide formulation developed epitope specific IgG1 antibodies at a serum titer greater than 1:100. Both Pep 11 and Pep 64 composite antigens are capable of potent stimulation of serum antibodies to influenza. Composite antigen sequence TB Pep 2 (comprised of influenza Pep 11 and TB Pep 1) when given to mice induced antibodies to influenza and influenza epitopes and also to the MTB heat shock protein.

Example 8

ICR mice and cotton rats were immunized with 1 µg of unconjugated composite influenza peptide vaccine (influenza HA, HA, and NA epitopes; Pep 11; SEQ ID 25, and M1 and M2e epitopes with a T-cell epitope; Pep 5906; SEQ ID No: 27) formulated with ALFQ by intramuscular, or intradermal routes (cotton rats were given both intramuscular, or Intradermal injections). Both routes of administration induced serum IgG antibodies that bound to groups 1 and 2 influenza viruses (Flu A California H1N1/pdm09 and Flu A Hong Kong H3N2/4801/2014). In addition, 1 µg of composite influenza vaccine formulated in ALFQ induced neutralizing antibodies against both influenza viruses given by Intradermal and Intramuscular routes. These data demonstrate that composite influenza peptide vaccines formulated in ALFQ induced a strong immune response at a very low dose without conjugation to a carrier and when administered by different routes of immunization. This provides an advantage in efficiency of manufacturing and decreased cost of production. Low dose Intradermal administration may also decrease cost of vaccines and be more useful for mass global immunization of humans and for immunizing animals such as birds and pigs.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. An immunogenic antigen comprised of:
a contiguous peptide containing one or more bacterial epitopes and one or more influenza epitopes, and
a T cell stimulating epitope and/or an adjuvant,
wherein the one or more bacterial epitopes are selected from the group consisting of cell wall epitopes of Mycobacteria, and the one or more influenza epitopes are selected from the group consisting of epitopes of hemagglutinin (HA), neuraminidase (NA) and matrix proteins of influenza virus, wherein the contiguous peptide comprises the sequences of one or more of SEQ ID NOs. 1-20 and one or more of SEQ ID NOs. 25-28, or the sequence of one or more of SEQ ID NOs. 9-17 and 20-23.

2. The immunogenic antigen of claim 1, wherein the Mycobacteria comprises *M. tuberculosis, M. bovis,* or *M. smegmatis.*

3. The immunogenic antigen of claim 1, wherein the epitope of *Mycobacteria* comprises an epitope of peptidoglycan, alpha crystalline protein, heat shock protein, arabinogalactan protein, glycine-rich protein, proline-rich protein, pseudopeptidoglycan, lipoteichoic acid, or lipopolysaccharide.

4. The immunogenic antigen of claim 1, wherein the T cell stimulating epitope comprises detoxified tetanus toxin, tetanus toxin heavy chain proteins, detoxified diphtheria toxin, diphtheria toxoid, natural CRM, recombinant CRM, tetanus toxoid, *Pseudomonas* exoprotein A, *Pseudomonas aeruginosa* toxoid, *Bordetella pertussis* toxoid, *Clostridium perfringens* toxoid, *Escherichia coli* heat-labile toxin B subunit, *Neisseria meningitidis* outer membrane complex, Hemophilus influenzae protein D, Flagellin Fli C, Horseshoe crab Haemocyanin, or fragments, derivatives, or modifications thereof.

5. The immunogenic antigen of claim 1, wherein the adjuvant comprises Freund's, a liposome, saponin, lipid A, squalene, liposomes adsorbed to aluminum hydroxide, liposomes containing QS21 saponin, liposomes containing QS21 saponin and adsorbed to aluminum hydroxide, liposomes containing saturated phospholipids, cholesterol, and/or monophosphoryl, ALFQ, ALFA, AS01, and/or modifications or derivatives thereof.

6. An immunogenic antigen comprised of an epitope of peptidoglycan, alpha crystalline protein or heat shock protein of *Mycobacteria*, plus a mimotope of HA, NA, or M2e protein of Influenza virus, further comprising CRM as a T cell stimulating epitope and/or ALFQ as an adjuvant, wherein the contiguous peptide comprises the sequences of one or more of SEQ ID NOs. 1-20 and one or more of SEQ ID NOs. 25-28.

7. An immunogenic antigen comprised of an epitope of peptidoglycan, alpha crystalline protein or heat shock protein of *Mycobacteria*, plus a mimotope of an epitope of peptidoglycan, alpha crystalline protein or heat shock protein of *Mycobacteria*, further comprising CRM as a T cell stimulating epitope and/or ALFQ as an adjuvant, wherein the contiguous peptide comprises the sequences of one or more of SEQ ID NOs. 1-20 and one or more of SEQ ID NOs. 25-28.

8. A vaccine comprising the antigen of claim 1.

9. The vaccine of claim 8, which contains a liposome-based adjuvant.

10. The vaccine of claim 9, wherein the liposome-based adjuvant comprises ALFQ.

11. The vaccine of claim 8, which contains detoxified tetanus toxin, tetanus toxin heavy chain proteins, detoxified diphtheria toxin, diphtheria toxoid, natural CRM, recombinant CRM, or tetanus toxoid as the T cell stimulating epitope.

12. An immunogenic antigen comprised of:
a contiguous peptide containing one or more bacterial epitopes and one or more influenza epitopes, wherein the contiguous peptide comprises the sequences of one or more of SEQ ID NOs. 1-8, 14, 15, 18-20, 22, 25 and 26.

13. The immunogenic antigen of claim 12, further comprising a T cell epitope.

14. The immunogenic antigen of claim 12, further comprising an adjuvant.

15. The immunogenic antigen of claim 12, wherein the one or more bacterial cell wall epitopes are from *Mycobacteria*.

16. The immunogenic antigen of claim 15, wherein the *Mycobacteria* comprises *M. tuberculosis, M. bovis,* or *M. smegmatis.*

17. The immunogenic antigen of claim 15, wherein the epitope of *Mycobacteria* comprises an epitope of peptidoglycan, alpha crystalline protein, heat shock protein, arabinogalactan protein, glycine-rich protein, proline-rich protein, pseudopeptidoglycan, lipoteichoic acid, or lipopolysaccharide.

18. A vaccine comprising the antigen of claim 12.

19. The vaccine of claim 18, which contains a liposome-based adjuvant.

20. The vaccine of claim 19, wherein the liposome-based adjuvant comprises ALFQ.

21. An immunogenic antigen comprised of:
a contiguous peptide containing one or more bacterial epitopes and one or more influenza epitopes, wherein the contiguous peptide comprises the sequences of one or more of SEQ ID NOs. 9-13, 16, 17, 21, 23, 27, and 28.

22. The immunogenic antigen of claim 21, further comprising an adjuvant.

23. The immunogenic antigen of claim 21, wherein the one or more bacterial cell wall epitopes are from *Mycobacteria*.

24. The immunogenic antigen of claim 23, wherein the *Mycobacteria* comprises *M. tuberculosis, M. bovis*, or *M. smegmatis*.

25. The immunogenic antigen of claim 23, wherein the epitope of *Mycobacteria* comprises an epitope of peptidoglycan, alpha crystalline protein, heat shock protein, arabinogalactan protein, glycine-rich protein, proline-rich protein, pseudopeptidoglycan, lipoteichoic acid, or lipopolysaccharide.

26. A vaccine comprising the antigen of claim 21.

27. The vaccine of claim 26, which contains a liposome-based adjuvant.

28. The vaccine of claim 27, wherein the liposome-based adjuvant comprises ALFQ.

* * * * *